United States Patent
Yabe

(10) Patent No.: US 6,850,636 B1
(45) Date of Patent: Feb. 1, 2005

(54) SURFACE INSPECTION SYSTEM

(75) Inventor: Tomoyoshi Yabe, Aichi (JP)

(73) Assignee: Nichiha Corporation, Nagoya (JP)

( * ) Notice: Subject to any disclaimer, the term of this patent is extended or adjusted under 35 U.S.C. 154(b) by 0 days.

(21) Appl. No.: 09/578,038

(22) Filed: May 25, 2000

(30) Foreign Application Priority Data

May 25, 1999 (JP) .......................................... 11-144912
Jun. 9, 1999 (JP) .......................................... 11-162471

(51) Int. Cl.$^7$ .............................................. G06K 9/00
(52) U.S. Cl. ...................................... 382/141; 382/108
(58) Field of Search ................................ 382/107, 108, 382/141, 151, 152, 142–145, 147; 348/87, 94, 95, 134

(56) References Cited

U.S. PATENT DOCUMENTS

| | | | | |
|---|---|---|---|---|
| 4,519,041 A | * | 5/1985 | Fant et al. | 382/141 |
| 4,525,741 A | * | 6/1985 | Chahal et al. | 348/255 |
| 4,817,177 A | * | 3/1989 | Shimizu | 382/276 |
| 5,917,602 A | * | 6/1999 | Bonewitz et al. | 356/614 |
| 6,081,613 A | * | 6/2000 | Ikurumi et al. | 382/147 |
| 6,421,458 B2 | * | 7/2002 | Michael et al. | 382/151 |

FOREIGN PATENT DOCUMENTS

| | | | | |
|---|---|---|---|---|
| JP | 63-120060 | 5/1988 | | |
| JP | 4-27810 | 1/1992 | | |
| JP | 4-46749 | 2/1992 | | |
| JP | 5-166025 | 7/1993 | | |
| JP | 8-75666 | 3/1996 | | |
| JP | 08075666 | * 3/1996 | .......... | G01N/21/88 |
| JP | 9-11090 | 1/1997 | | |
| JP | 9-160982 | 6/1997 | | |
| JP | 09160982 | * 6/1997 | .......... | G06F/17/60 |

OTHER PUBLICATIONS

Japanese Office Action and abridged translation regarding patent application No.: Hei 11–1144912.

* cited by examiner

*Primary Examiner*—Mehrdad Dastouri
*Assistant Examiner*—Virginia Kibler
(74) *Attorney, Agent, or Firm*—Shook, Hardy & Bacon LLP

(57) ABSTRACT

An inspection system which enables even the production control section located at a remote place to trace and inspect the changing process of the external appearance, after undergoing through each manufacturing process, of a great number of work boards that have been placed on a continuous work line. According to this inspection system, the moving velocity of work board being transferred by means of a transfer roller is measured by a rotary pulse encoder, and the sampling rate of a CCD line sensor camera is controlled to obtain a surface image data of the moving work board.

2 Claims, 21 Drawing Sheets

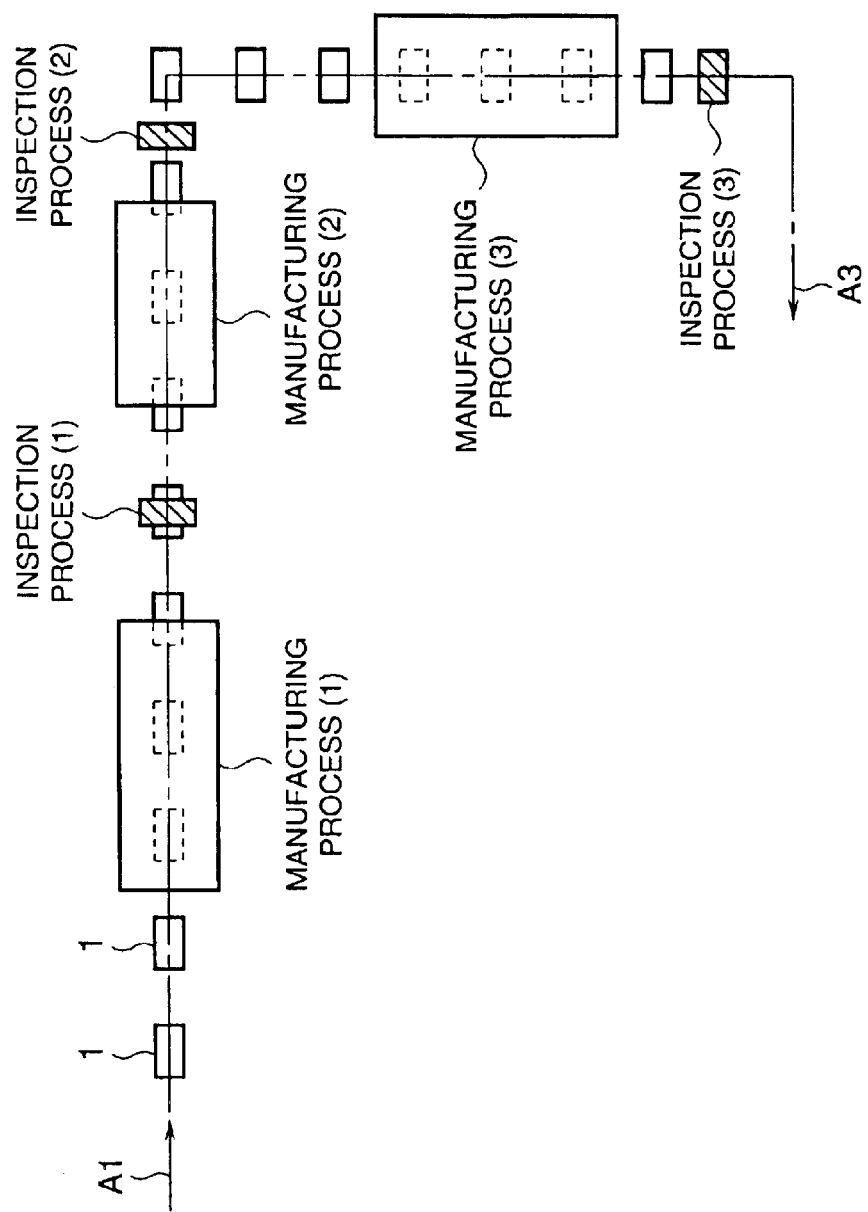

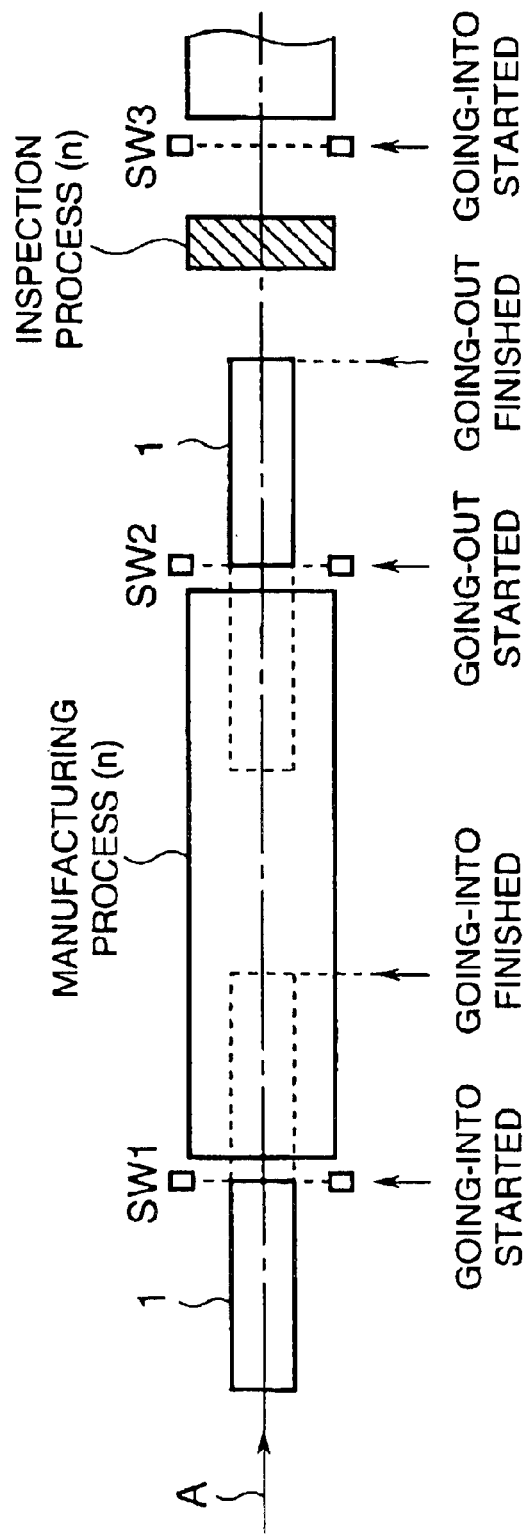

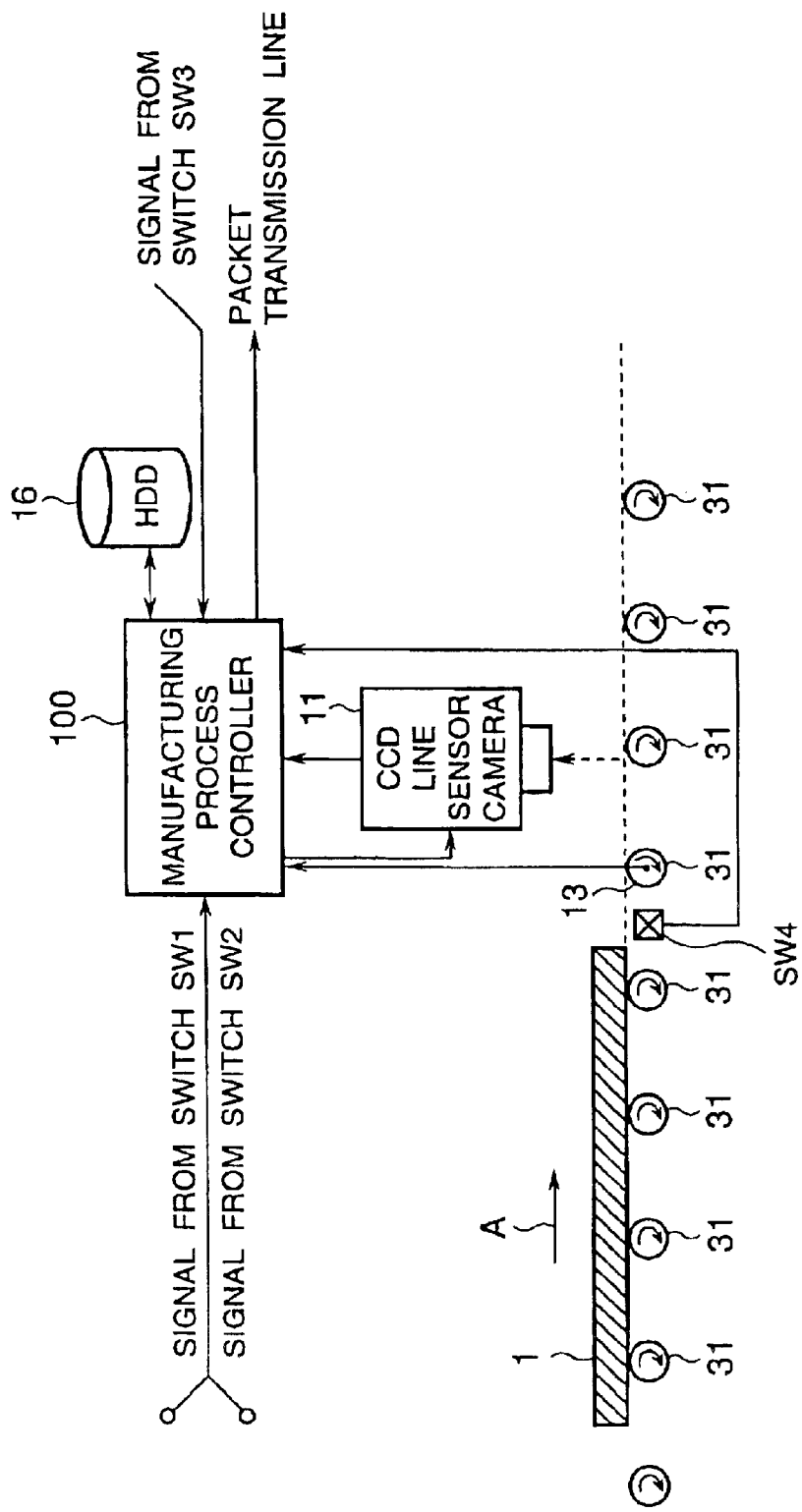

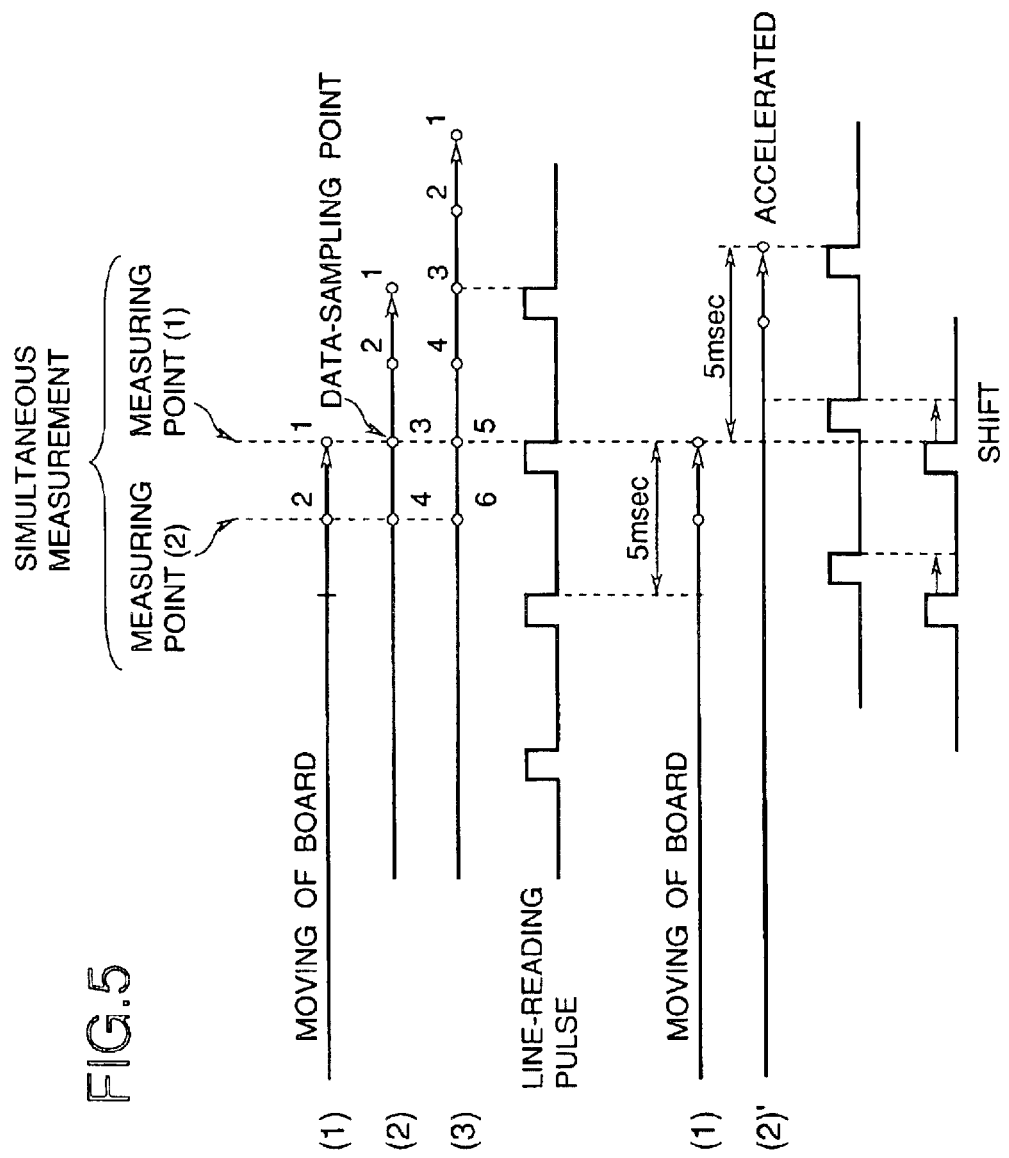

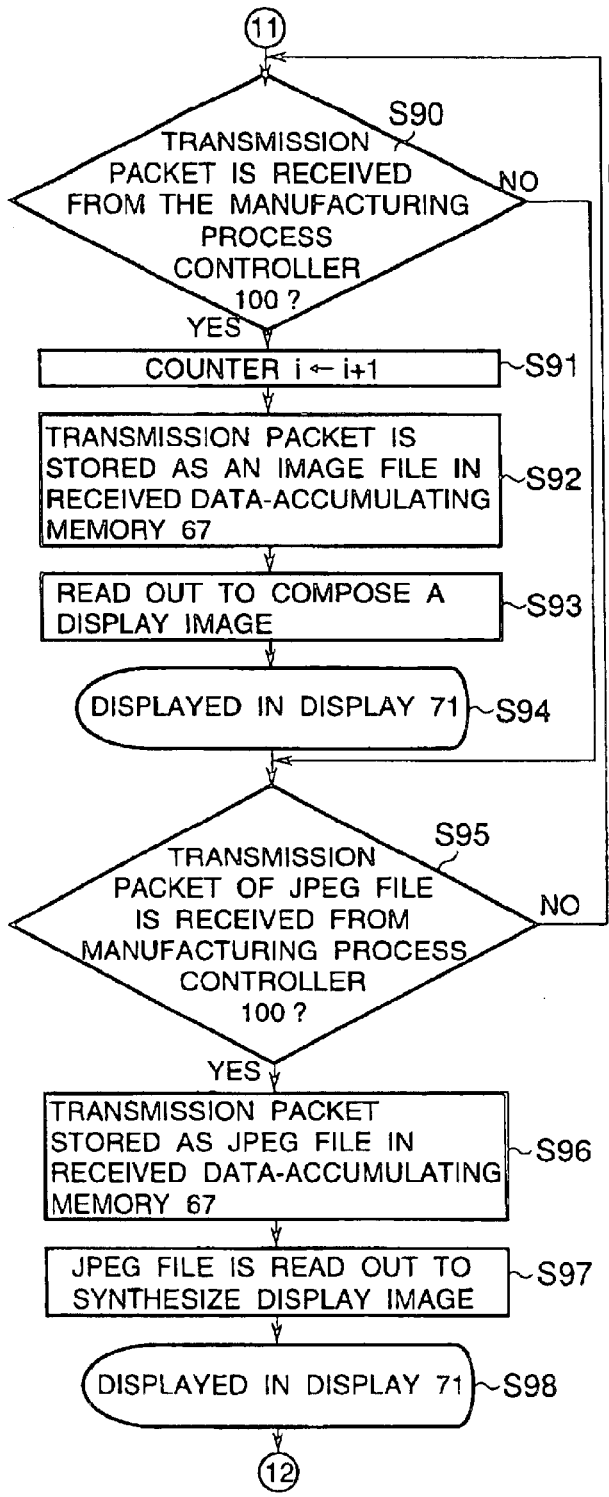
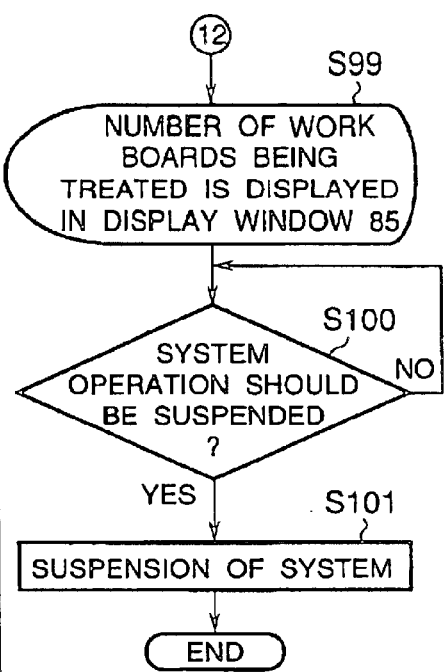

SURFACE INSPECTION SYSTEM

BACKGROUND OF THE INVENTION

1. Field of the Invention

The present invention relates to an inspection system for work boards (boards to be worked) such as building boards, and in particular, to an inspection system for identifying work boards and automatically inspecting the surface of work boards that have been treated in each manufacturing process.

2. Description of the Related Arts

In a conventional continuous work line handling work boards, for instance, the shape and color tone of a semi-finished product are frequently caused to change on every occasions after finishing each manufacturing process. For example, in a continuous coating line of building boards, the color tone of the building board is caused to apparently change upon finishing each manufacturing process even if the original shape of the building board or work board is not changed.

As mentioned above, the external appearance of semi-finished product to be shown after finishing each manufacturing process in a continuous work line is frequently caused to change more or less as compared with the external appearance of the same semi-finished product obtained in the previous manufacturing processes.

In such cases, instead of performing an inspection of individual building boards at each manufacturing process thereof, an inspection process is usually performed at the final stage of manufacturing process so as to perform the inspection on the finally finished product. The building board that has passed through this inspection is then usually marked with a specific manufacturer's serial number so as to make it possible to distinguish each building board by this serial number. The reason for performing the inspection at the final stage of manufacturing process may be attribute to the fact that it is very difficult to uniformly impose inspection conditions at a point midway through the manufacturing process. For example, the object of inspection may not be moving along a fixed location of transferring line, or the object of inspection just transferred from a drying process may inevitably undergo a physical or chemical change due to a thermal change with time. Namely, the fact that the object of inspection is not necessarily in a stable state at the midway point of the manufacturing process is one reasons for not performing the inspection at the midway point.

However, if an unexpected inappropriate coating treatment is happened to be performed in a continuous coating line to thereby generate a non-uniformity of coating, an inappropriately coated semi-finished products will be unavoidably subjected to the next working process since it is impossible to find out such an accident unless the coated state is always watched. As a result, it will bring about a serious problem that defective building boards will be continuously produced in large quantities.

Even so, it may be severe to entrust an operator with such a watching operation, and moreover, such an idea is undesirable in promoting the labor saving.

On the other hand, a line monitoring system using a television camera is widely adopted in a manufacturing plant. However, most of them are employed for the purpose of watching if there is any abnormal moving of work boards. Namely, there is no case wherein the line monitoring system is employed for the purpose of inspecting any change in the external appearance or color tone of work boards at each manufacturing process.

Of course, there is a case wherein a monitoring system is employed for watching various controlling items such as temperature, humidity and pressure at each manufacturing process. However, as far as the inspection and evaluation of semi-finished product obtained from each process are concerned, it is inevitable at present to rely on the operator's naked eyes.

Meanwhile, when any defect is found on a finished product and the cause thereof is attempted to trace, the manufacturing plant as well as the produced date of the defective product can be identified from the specific manufacturer's serial number thereof. However, it would be impossible to trace the specific manufacturing conditions under which the product is produced at each manufacturing process, so that it would be impossible to trace the fundamental cause for the production of the defective product.

SUMMARY OF THE INVENTION

The present invention has been made to solve the aforementioned problems. Therefore, an object of the present invention is to provide an inspection system which enables even in the production process even at remote locations and allows one to trace and inspect how large the external appearance of a great number of work boards, that have been placed on a continuous work line, will be changed after undergoing each manufacturing process.

Another object of the present invention is to provide an inspection system which is capable of identifying each individual work board and of recording the manufacturing conditions of the individual work board even if the external appearance of that work board is liable to change in the manufacturing process along a continuous work line.

Namely, according to the present invention, there is provided an inspection system, which comprises a line sensor for one-dimensionally imaging an elongated work boards, a velocity-measuring means for measuring a moving velocity of the work board, a sampling control means for controlling the sampling of said line sensor on the basis of the moving velocity of the work board to be measured by said velocity-measuring means, and an image-composing memory for composing an output of said line sensor to generate a two-dimensional image data.

The velocity-measuring means is designed to measure the rotational velocity of a transferring roller for transferring the work board, thus making it possible to easily and accurately measure the moving velocity of the work board.

The inspection system may be further provided with a controlling means to correct the sampled image data based on the extent to which the work board is slanted or moved out of a normal position, thereby making it possible to easily compare the image data with that of image data of a standard work board or other work board.

Further, the inspection system may be further provided with a data transmitting means for assigning a transmission channel to every work board and assembling the image data into data-packets so as to transmit them, thereby making it possible to effectively transmit the image data without causing a collision between many packets of data.

When the inspection system is provided with a detecting means for detecting a work board on a work line, time-measuring means for measuring a detected time when the work board is detected by said detecting means, and identifying means for identifying the work board using said detected time measured by said time-measuring means, it becomes possible to easily distinguish individual work board which is generally difficult to distinguish from others by the external appearance.

The detecting means is designed to detect the work board going into a prescribed manufacturing process and the work board going out from said prescribed manufacturing process, thus making it possible to facilitate the delivery of an identification information between a couple of successive processes.

The detecting means detects a leading and a trailing end portion of the work board to be transferred, thus making it possible to facilitate the delivery of an identification information between a couple of successive processes.

The identifying means is also designed to identify the work board by way of a manufacturing process and the time when the work board has passed through said manufacturing process, thus making it possible to identify the work board in relative to each manufacturing process, i.e. by referring to the specific manufacturing process and time the work board has passed through.

The identifying means identifies the image data of the work board which has been gone out from a manufacturing process by way of said manufacturing process and the time when the work board has passed through said manufacturing process, thus making it possible to identify the image data of the work board after each manufacturing process.

BRIEF DESCRIPTION OF THE DRAWINGS

A more complete appreciation of the invention and many of the attendant advantages thereof will be readily understood by reference to the following detailed description and the accompanying drawings, wherein:

FIG. 1 is a top view illustrating schematically a part of the continuous work line which can be suitably applied to the inspecting system of work board according to one embodiment of the present invention;

FIG. 2 is an enlarged schematic view illustrating a main portion of the continuous work line shown in FIG. 1;

FIG. 3 is a schematic view illustrating the arrangement of the inspecting process portion;

FIG. 5 is a diagram illustrating changes of line reading rate;

DESCRIPTION OF THE PREFERRED EMBODIMENTS

Figure 4A:
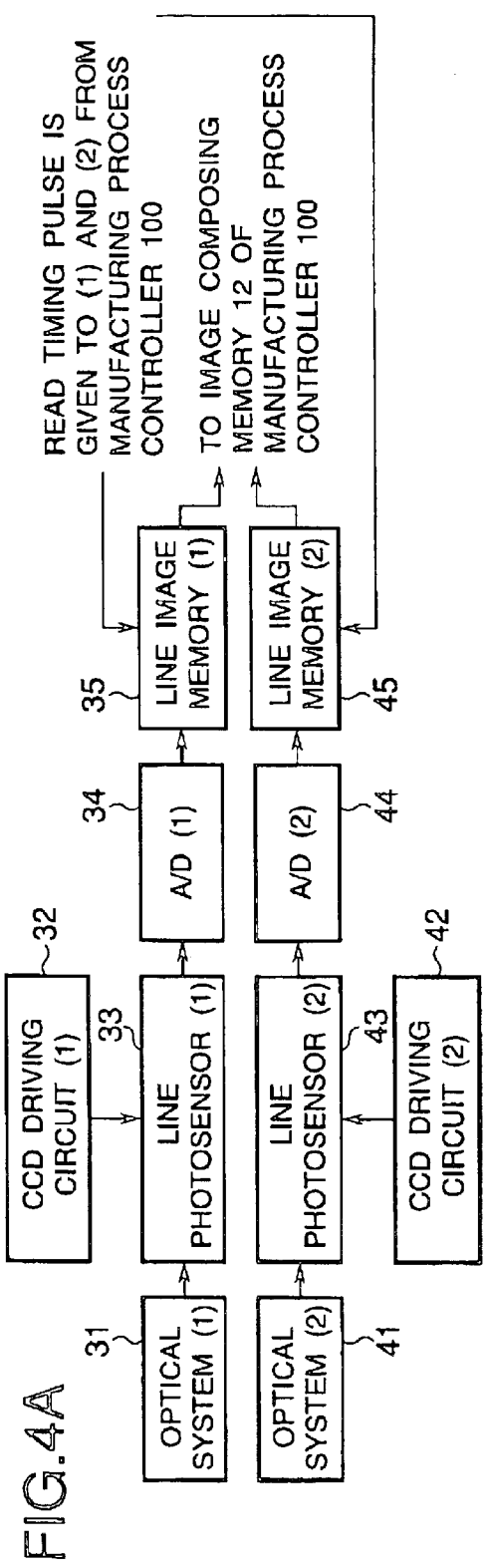
FIG. 4A is a block diagram illustrating an internal configuration of a CCD line sensor camera shown in FIG. 3.

Preferable embodiments of the present invention will be explained in detail with reference to the drawings.

FIG. 1 is a top view illustrating automatically a part of the continuous work line which can be suitably applied to the inspecting system of work board according to one embodiment of the present invention. In the following explanation, a building board 1 is exemplified as the work board. A raw board 1 of the building board goes at first into a manufacturing process (1) in the direction of an arrow A1. After finishing a working in the manufacturing process (1), the work board is inspected at an inspection process (1) and then, moved to the next manufacturing process (2). After finishing treatment in the manufacturing process (2), the work board is inspected at an inspection process (2) and then, changes the moving direction to move the next manufacturing process (3). After finishing a working in the manufacturing process (3), the work board is inspected at an inspection process (3) and then, further turned and delivered in the direction of an arrow A3 for subjecting it to the next manufacturing process.

A great number of work boards 1 are intermittently fed at predetermined intervals into the continuous working line in this manner. After finishing a predetermined number of treatment processes, the work boards ultimately exit the continuous working line. During these working processes, the work boards are moving individually through the continuous transferring line.

There is an upper limit with respect to the total number of work boards that can be placed on the transferring line as the transferring lines are steadily operated.

On the other hand, as far as each manufacturing process is concerned, the time when the work board 1 goes into or enters the prescribed manufacturing process as well as the time when the same work board 1 goes out from or exits said prescribed manufacturing process can be represented by an absolute value of time of working (it means that the time elapsing minute by minute would never go back) which is applied to individual work board 1 in said prescribed manufacturing process. The work board 1 may enter and exit the manufacturing process at the same moment in other manufacturing processes. However, as far as a single specific manufacturing process is concerned, the time when the individual work board enters and exits the manufacturing process is a value peculiar to this individual work board 1. This will be specifically explained below.

For example, assuming that the work line is operated in a steady state, when a work board 1 enters at 10:00 in the manufacturing process 1 and then, exits from the manufacturing process 1 at 10:10 as scheduled, this 10 minutes of working during which this work board 1 has been treated in the manufacturing process 1 can be represented by three data (process number=1; entry time=10:00; and exit time=10:10). From these data, it can be shown that this work board 1 lies in the manufacturing process 1 for receiving a treatment during this period of time.

Supposing that this work board 1 exits at 10:15, there is a possibility that trouble of some kind may have occurred in this or other manufacturing process. Specifically, when this work line is temporarily suspended, due to some problem that has occurred in this manufacturing process, or in another manufacturing process, a delay would be caused in the exit time. Therefore, it is impossible to determine if the work board 1 to be inspected has been really worked in a steady state, knowing only the exit time.

FIG. 2 is an enlarged schematic view illustrating a main portion of the continuous work line shown in FIG. 1. When the detecting light emitted from a photoelectric switch SW1 is intercepted by the leading end portion of work board 1 as the work board 1 is moved in the direction of an arrow A, the photoelectric switch 1 detects that the work board 1 goes into or enters a manufacturing process (n). When the light emitted from a photoelectric switch SW1 is not intercepted by the trailing end portion of work board 1, the photoelectric switch SW1 detects that the work board 1 going into the manufacturing process (n) has ended and an exit finish time tie (n) is measured and a scheduled exit starting time tees (n) is calculated. When the detecting light emitted from a photoelectric switch SW2 is intercepted by the leading end portion of work board 1, the photoelectric switch SW2 detects that the work board 1 exiting the manufacturing process (n) is started, and an exit starting time tes (n) is measured so as to compare it with the scheduled exit starting time tees (n), thereby checking that the work board 1 has exited. When the detecting light emitted from a photoelectric switch SW2 is not intercepted by the trailing end portion of work board 1, the switch SW2 detects that the work board 1 exiting the manufacturing process (n) has ended and the exit finish time tee (n) is measured and a scheduled entering-starting time teis (n+1) to the next manufacturing process (n+1) is calculated. When the detecting light emitted from a photoelectric switch SW3 is intercepted by the leading end portion of work board 1 after the work board 1 has passed through an inspection process (n) of the manufacturing process (n), the photoelectric switch SW 3 detects that the work board 1 going into the manufacturing process (n+1) is started, and a going-into-or entering starting time tis (n+1) is measured so as to compare it with the scheduled entry starting time teis (n+1), thereby checking that the work board 1 has entered.

When the entering time is measured and the work board 1 has exited at a scheduled exit starting time in this manner, an inspection or an acquisition of image data is performed. Thereafter, when the work board 1 is moved into the next manufacturing process at a scheduled time after finishing the inspection in the previous process, it is determined that the work board 1 is ready to receive the next treatment.

As explained above, the measurement of the entry time of the work board 1, the measurement of the exit time of the work board 1, the determination of whether the work board 1 has actually left the manufacturing process at a scheduled exit time measurement based on the entry time, the execution of inspection following the manufacturing process, and the determination of whether the work board 1 has actually entered the next manufacturing process at a scheduled entry time measurement based on the unloading time are all designed to be executed by "the manufacturing process controller" for controlling this manufacturing process.

Since the scheduled exit time and the scheduled entry time for the next manufacturing process are all calculated estimated values, some degree of tolerance should be allowed in the determination of the actual time in view of possibility of generating a slight degree of error in moving time of the work board 1 due to various factors such as a slippage of a transferring means.

The individual work board 1 specified as being a work board 1 worked in a prescribed manufacturing process as mentioned above is treated as corresponding in the relationship of one to one with the surface image data (a stationary image data as explained hereinafter) of the work board 1, which can be obtained by the working in this manufacturing process. Therefore, this surface image data is identified by the following "board-specifying key" so as to be stored in a recording media. The board data to be specified by this board-specifying key are as follows.

A board-specifying key 1: d1 (process 1; going-into time ti(1), going-out time te(1));

A board-specifying key 2: d2 (process 2; going-into time ti(2), going-out time te(2));

- - - ;

A board-specifying key n: dn (process n; going-into time ti(n), going-out time te(n));

(n=1, 2, 3, - - - N; wherein N is an optional integer corresponding to the number of processes in the work line)

The surface image data Pn (n=1, 2, 3, - - - N) obtained from the board data n which has been specified by the aforementioned board-specifying key is stored in a recording media in the relationship of one to one.

According to this embodiment, the accumulation of image data on the surface of the work board 1 is intended to be recorded in compression (for example, JPEG) in a hard disk HDD to be controlled by each manufacturing process controller. Accordingly, the surface image of individual work board 1 thus recorded can be respectively retrieved as an image data file.

FIG. 3 is a schematic view illustrating the arrangement of the inspecting process portion. The manufacturing process controller 100 (to be explained in detail with reference to FIG. 10) is designed to identify each work board 1 on the basis of the time obtained respectively from the photoelectric switch SW1 (for measuring the entry time of the previous manufacturing process), the photoelectric switch SW2 (for measuring the exit time of the previous manufacturing process), and the photoelectric switch SW3 (for measuring the entry time of the next manufacturing process). The work board 1, transferred from the previous manufacturing process by means of the transferring rollers 31, is detected by a photoelectric switch SW4, and then, the transferring velocity thereof is detected by a rotary pulse encoder 13. Based on this transferring velocity, the sampling rate is determined, and the surface of the work board 1 is one-dimensionally imaged by means of a CCD line sensor camera 11. The image data obtained by this imaging is accumulated occasionally in a hard disk HDD 16. As a result, even if the work board 1 is moving at a varying speed, it is possible to determine the sampling timing of image data on the basis of output obtained through the measurement by the rotary pulse encoder 13 attached to the transferring roller 31 for measuring the rotational velocity of the transferring roller 13 which is installed immediately below or immediately in front of the CCD line sensor camera 11 positioned over the transferring zone of the work board 1.

As for the start and suspension of sampling of image data, they can be determined by means of the photoelectric switch SW4 which is disposed for detecting the passing of the work board 1 through a position immediately below the CCD line sensor camera 11.

Figure 4B:
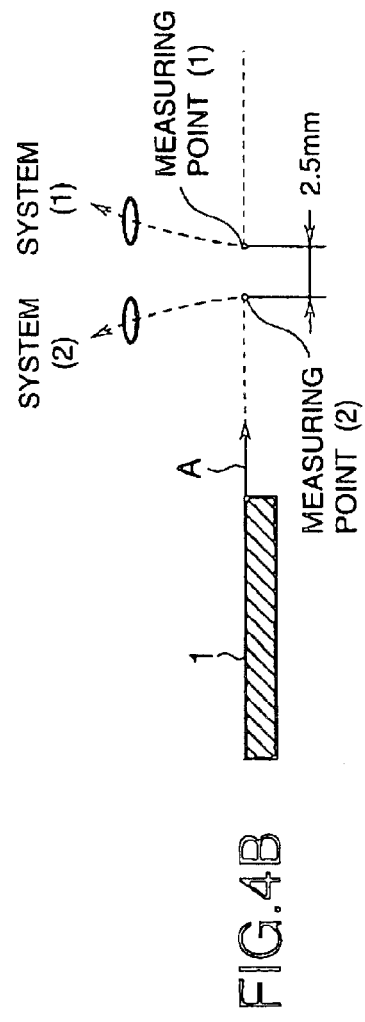
FIG. 4B is a diagram illustrating the measuring points.

FIG. 4A is a block diagram illustrating an internal configuration of the CCD line sensor camera 11 shown in FIG. 3. This CCD line sensor camera 11 is provided with two systems for reading, i.e. a system (1) for an odd number line and a system (2) for an even number line, thereby enabling it to enhance the resolution. The imaged data is fed from each reader to an analog-digital converter 34 (A/D(1), and 44 A/D(2)), respectively, in which they are converted into digital form. As shown in FIG. 4B, the measuring point (1) and the measuring point (2) are positioned away from each other along the transferring or movement direction of the work board 1, thus in the transferring direction A. These measuring points (1) and (2) are given to be imaged by an optical system (1) 31 and an optical system (2) 41, respectively. The results thus imaged are then photo-electrically converted by means of a line photosensor (1) 33 and a line photosensor (2) 43 which are to be driven using a CCD driving circuit (1) 32 and a CCD driving circuit (2) 42, respectively, as shown in FIG. 4A. The analog signals thus obtained through this photo-electric conversion are then converted into digital signals. Then, the RGB data of the odd number line is temporarily stored in a line image memory (1) 35, while the RGB data of the even number line is temporarily stored in a line image memory (2) 45, thereby enabling them to be transmitted to an image compressing memory 12 of the manufacturing process controller 100.

On this occasion, when the moving velocity of the work board 1 is assumed to be 60 m/min. (or 1 m/sec.) and the resolution to be 2.5 mm, since there are two line sensors, a line reading pulse will be generated every 5 msec. (2.5 (mm)×2/1 (mm/msec.)=5 msec.) (pulse rate is 200 PPS). This line reading pulse rate is adjusted in proportion to the moving velocity of the work board 1.

When the moving velocity of the work board 1 is accelerated, the line reading pulse rate is also accelerated. On the other hand, when the moving velocity of the work board 1 is decelerated, the line reading pulse rate is also decelerated. Therefore, even if the velocity of work board is varied, the line reading can performed with almost the same resolution by immediately conforming it to the varied velocity. In this case, it is advisable to determine in advance a relational expression between the rotational velocity of the transferring roller and the line reading pulse rate, thereby enabling the amount of shift of pulse to be adjusted according to this relational expression.

FIG. 5 is a diagram illustrating changes of line reading rate. When the moving velocity of the work board 1 is assumed to be 1 m/sec., at the initial moment (1), the reading of data-sampling points 1 and 2 is performed, respectively, at the measuring point (1) of the odd number line as well as at the measuring point (2) of the even number line. At the next moment (2) 5 msec after the initial moment (1), the reading of the data-sampling points 3 and 4 is performed respectively at the measuring point (1) as well as at the measuring point (2). Further, at the next moment (3) 5 seconds after the aforementioned moment (2), the reading of the data-sampling points 5 and 6 is performed respectively at the measuring point (1) as well as at the measuring point (2). Whereas, when the moving velocity of the work board 1 is accelerated faster than 1 m/sec., the work board 1 is caused to move a longer distance during this 5 seconds, so that the line reading pulse is required to be shifted so as to increase the sampling rate in order to make it possible to read with the same resolution as the previous moving velocity at the moment of (2)'.

Figure 6:
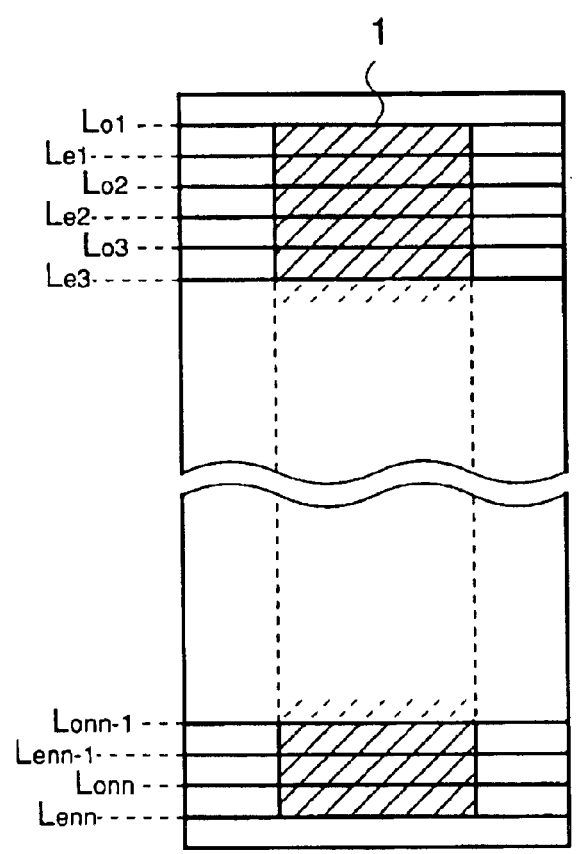
FIG. 6 is a diagram illustrating the accumulation of image data in an image-composing memory.
Figure 10:
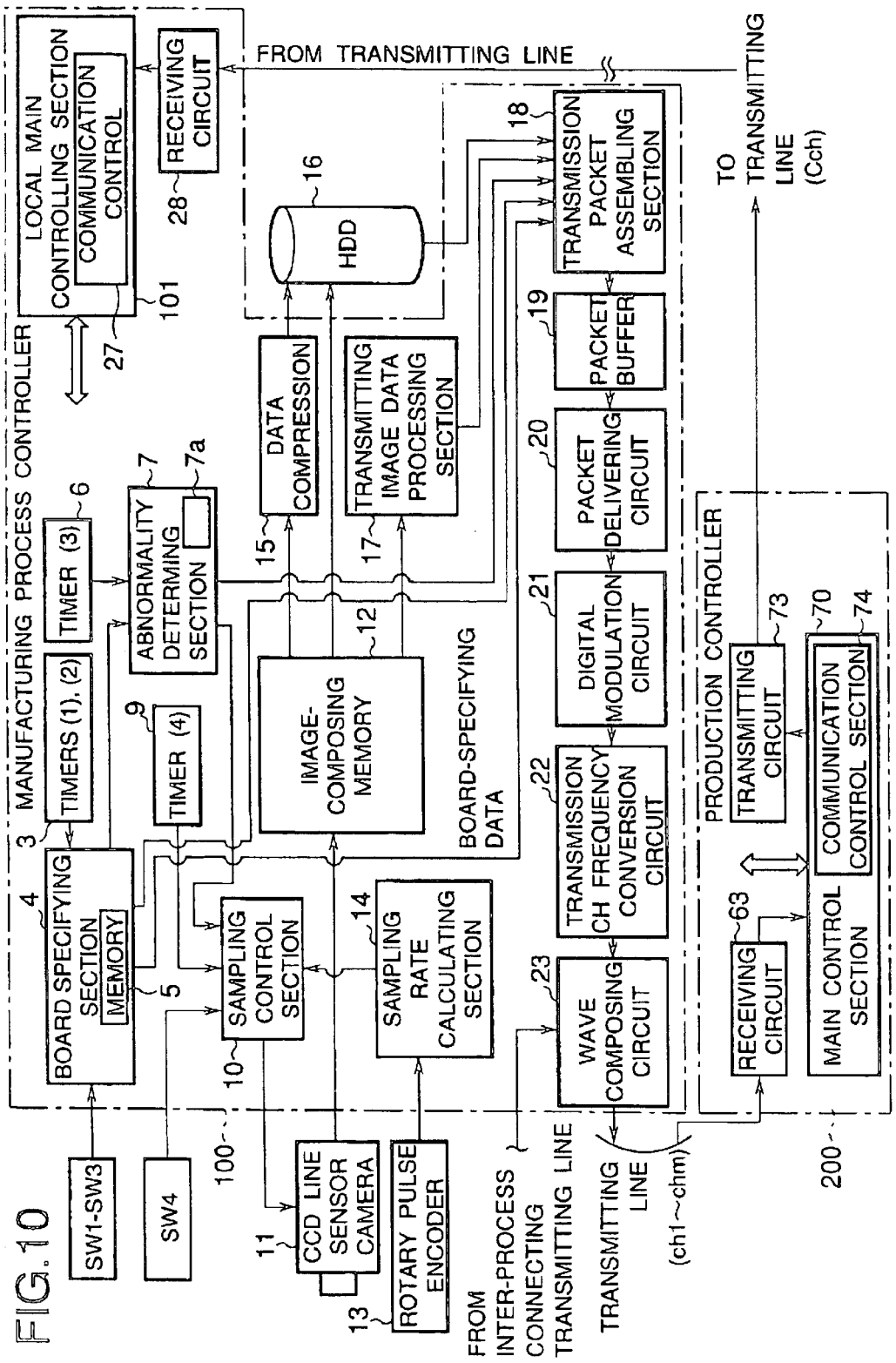
FIG. 10 is a block diagram illustrating the constructions of the manufacturing process controller and those of the production controller.

FIG. 6 is a diagram illustrating the accumulation of image data in an image-composing memory 12 (see FIG. 10). In this embodiment, only a R (red) signal is illustrated. However, this can be also applied to a G (green) signal as well as a B (blue) signal. Each line image memory 35 or 45 (see FIG. 4) is constituted on the FIFO (first-in first-out) basis and hence, the data can be read out according to the line-reading pulse and written in compression in the image-composing memory 12 of the manufacturing process controller 100. In this case, the odd number line data of row number nn, i.e. Lo1, Lo2, Lo3, - - - , Lonn and the even number line data of row number nn, i.e. Le1, Le2, Le3, - - - , Lenn are simultaneously and alternately written while changing the row in the memory 12. In this case, not only the board image data but also the background image data are simultaneously written in the memory 12. However, this problem can be corrected in a subsequent data processing. In this manner, a board image to be inspected can be composed.

Figure 7A:
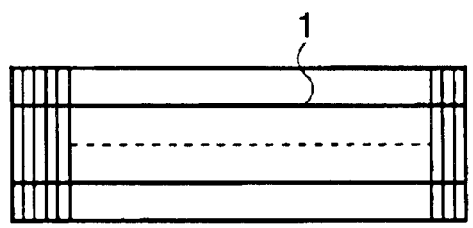
FIG. 7A is a case where a work board is not slanted.
Figure 7B:
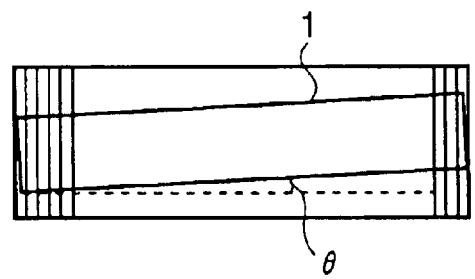
FIG. 7B is a case where a work board is slanted.
Figure 7C:
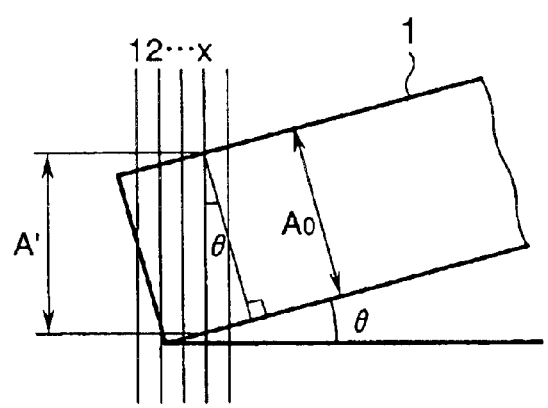
FIG. 7C is a diagram illustrating a method of calculating the angle of deviation.

FIG. 7A is a case where a work board is not slanted. Whereas, when the work board 1 slants by an angle of θ from the ordinary moving direction thereof, the image shown in FIG. 7B will be obtained. Since it is impossible to compare it with the standard work board 1 in this case, the angle of slant θ is calculated by a local main controlling section 101 (see FIG. 10) as shown in FIG. 7C. Namely, since there is the following relationship between the number Ao of pixels corresponding to the width of the work board 1 and the number A' of pixels forming the board on the data sampling line (A' is determined on the basis of the xth data sampling line as counted from the beginning, which is a line suitable for determining A'):

$$\cos θ = Ao/A',$$

the following relationship can be obtained:

$$θ = \cos^{-1}(Ao/A')$$

Based on the angle of slant θ thus obtained, the affine transformation is performed so as to obtain image data where the slant is corrected.

Figure 8A:
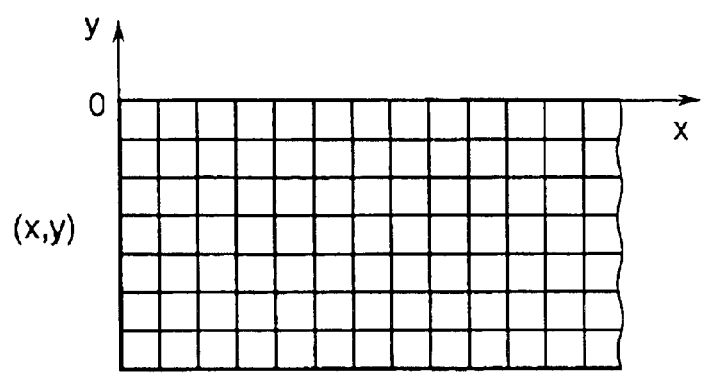
FIG. 8A is a X-Y coordinates of a work board.
Figure 8B:
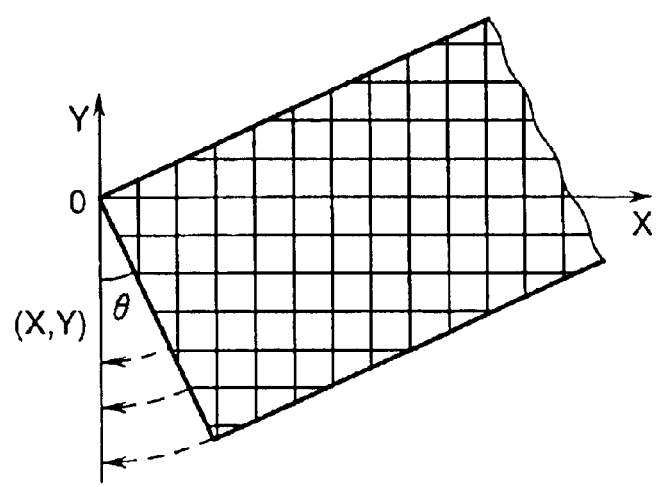
FIG. 8B is a diagram illustrating the position of a work board when the work board is slanted.

FIG. 8A is an X-Y coordinate representation of a work board. When the position (X, Y) is rotated by an angle of θ as the work board 1 is deviated by an angle of θ as shown in FIG. 8B so as to obtain the position (x, y) as shown in FIG. 8A, the following equations can be obtained.

$$x = X \cos θ + y \sin θ$$

$$y = -X \sin θ + Y \cos θ$$

In this manner, the sampling of board image data on an elongated board which is a moving object to be inspected can be performed accurately in a non-contact manner and at a high speed, and at the same time, when the image data obtained is compared with a standard board image data that has been recorded in advance. This offers easy detection whether or not the occurrence of abnormality has occurred.

The composed board image data thus obtained is compressed in conformity with JPEG and stored in a hard disk HDD 16. Each of the board image data thus recorded in a hard disk HDD 16 can be respectively read out by the use of the aforementioned board-specifying key.

Figure 9:
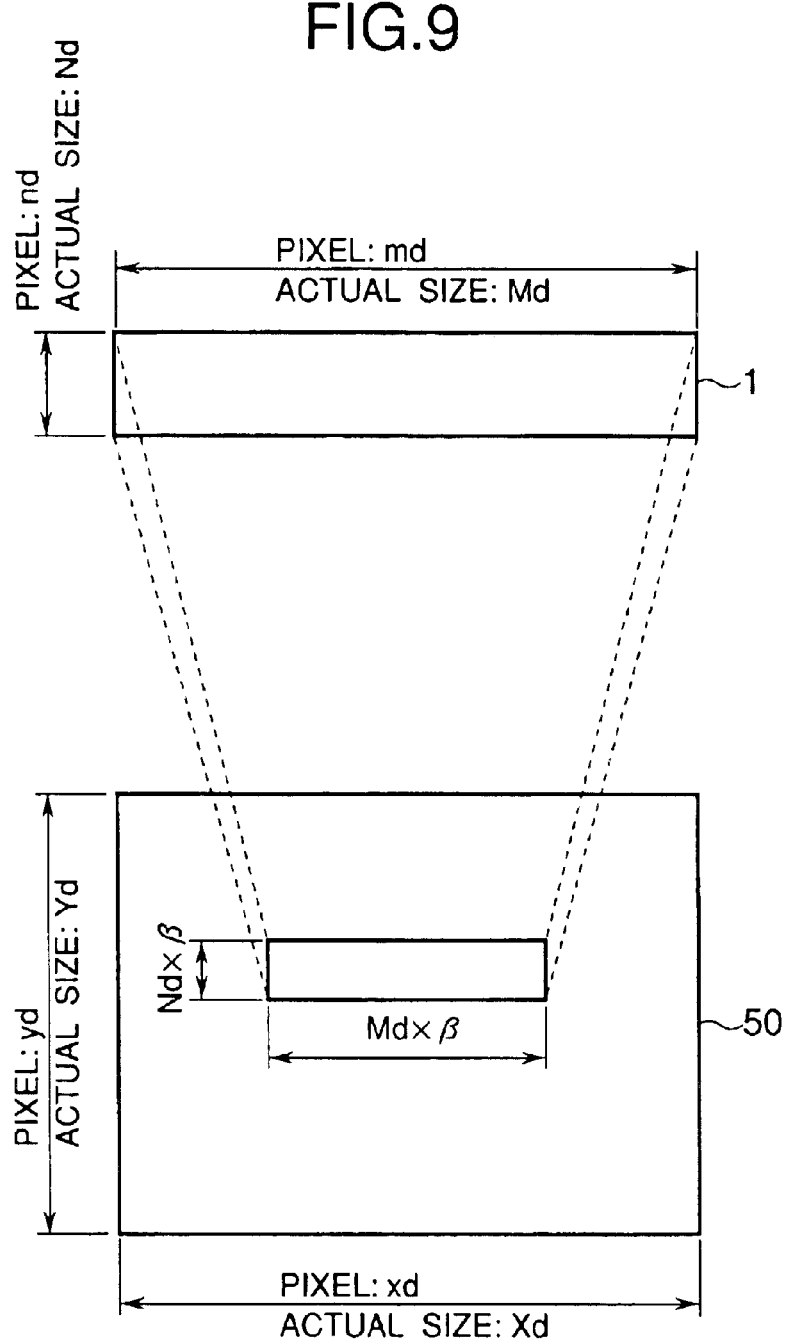
FIG. 9 is a diagram illustrating a relationship between a composed image data of a board and an image data to be displayed.

FIG. 9 is a diagram illustrating a relationship between the image data of a composed board (already corrected) and an image data to be displayed. The aforementioned composed board image data is then subjected to a data processing for enabling it to be transmitted to a production controller located at a remote place. Namely, the data compression is performed in order to reduce the aforementioned composed board image data to an image size suited for displaying it as a board image in a monitor display 71 (see FIG. 17) which is connected with the production controller. In this case, it is instructed by the production controller that "in what degree of resolution the image should be displayed?", so that the resolution of monitor itself to be actually displayed is taken into account. While the composed board image data is of high resolution for the purpose of inspection, the display image data is of standard resolution. If the composed board image data is; the number of pixel: md×nd; actual size: Md×Nd, while a monitor display 50 is; the number of pixel: xd×yd; corresponding actual display size: Xd×Yd, and if the display reduction ratio $\beta$, the actual display size becomes Md×$\beta$×Nd×$\beta$, and the image data is compressed in such a manner that md pixel and nd pixel become;

(Md×$\beta$)×(xd/Xd) and (Nd×$\beta$)×(yd/Yd), respectively.

FIG. 10 is a block diagram illustrating the constructions of the manufacturing process controller 100 and those of the production controller according to this embodiment. Detailed operation of these controllers will be explained in the flow chart shown in FIG. 11. The local main controlling section 101 provided with a communication control section 27 is designed to control entirely individual control module. The board specifying section 4 is designed to identify the individual work board 1 by the use of the photoelectric switches SW1 to SW3 (2) and the timers 3 (timers (1) & (2)), the result being stored in the memory 5. With respect to the work board 1 thus specified, an abnormal moving thereof is judged by an abnormality determining section 7 by the use of a timer 6 (timer (3)) also, the result being stored in a flag register 7a. The sampling control section 10 is designed to control the sampling of the CCD line sensor camera 11 by the use of the photoelectric switches SW4, the timer 9 (i.e., (4)) and the sampling rate corrected, on the basis of the pulse from the rotary pulse encoder 13, by a sampling rate calculating section 14. The image-composing memory 12 is designed to compose and store a corrected line image data fed from the CCD line sensor camera 11. A data compression section 15 is designed to compress the data as to store it in the hard disk HDD 16, and at the same time, controlling information is also stored in the hard disk HDD 16. A transmitting image data processing section 17 is designed to process the image data for transmission. A transmission packet assembling section 18 is designed to assemble the resultant image data into a transmission packet, which is then held by a packet buffer 19. The packet is subsequently delivered by a packet delivering circuit 20 and then subjected to a digital modulation at a digital modulation circuit 21 and to a frequency conversion for transmission at a transmission CH frequency conversion circuit 22. The resultant data is transmitted from a wave composing circuit 23 via a transmission line to the production controller 200.

On the other hand, the production controller 200 is constructed such that the data is received by a receiving circuit 63 and controlled at a main control section 70 provided with a communication control section 74, a controlling signal needed being subsequently delivered through a transmitting circuit 73 to a transmissing line. The wave composing circuit 23 is bidirectionally connected with an inter-process connection transmission line. As for the data transmissing system, it will be explained in detail with reference to FIG. 17.

Figure 11:
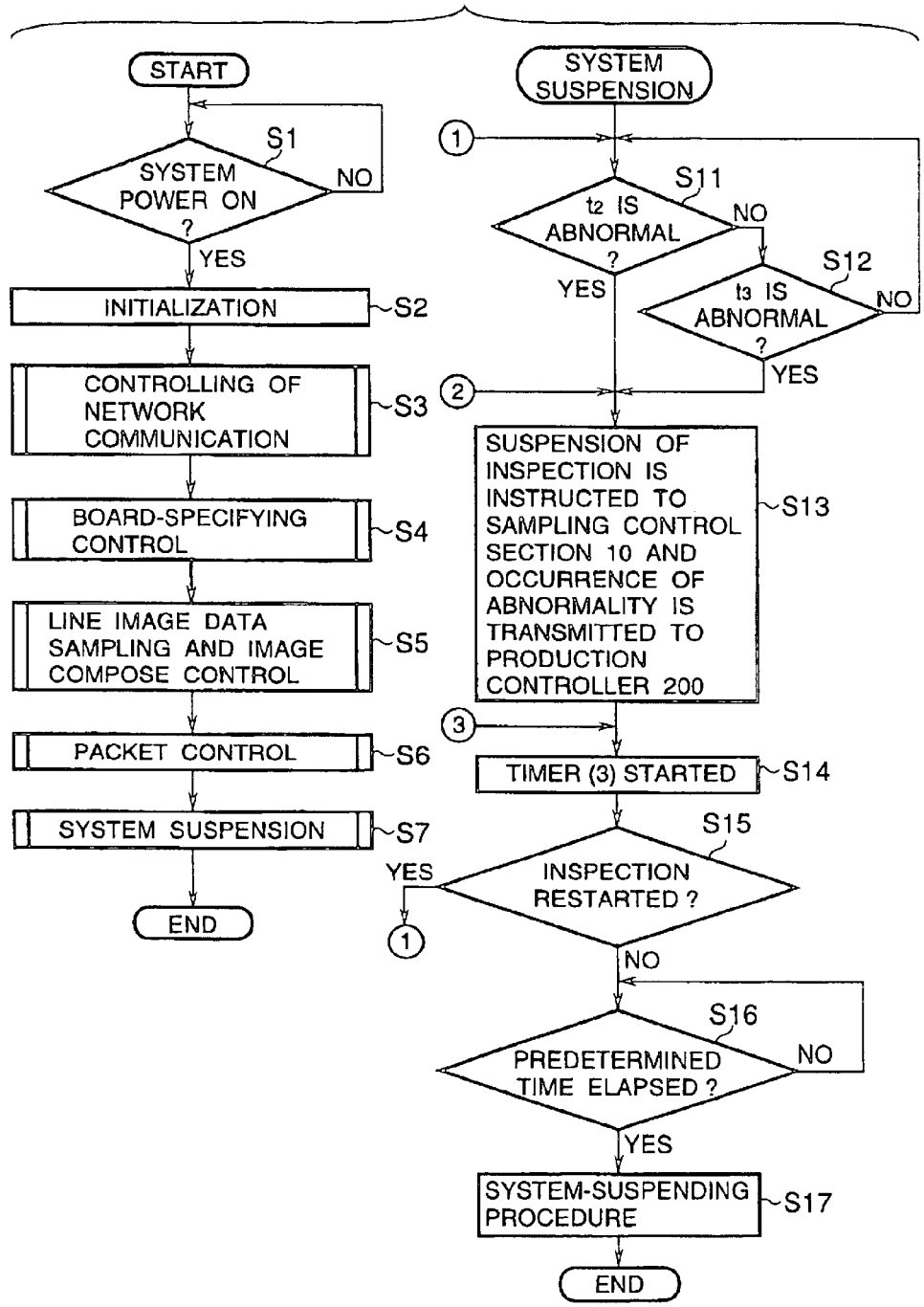
FIG. 11 is a flow chart indicating the operation of the manufacturing process controller.

FIG. 11 is a flow chart indicating the operation of the manufacturing process controller 100. First of all, it is determined if the system power source is ON (step S1). When the result is NO, the controller 11 forces the procedure to bring into a state of standby until the power switch is turned ON. If the result is YES, the initialization of the system is performed (step S2).

In the next step S3, the control of network communication is performed, and in the step S4, a board-specifying controlling is performed. In the step S5, a line image data sampling and an image compose controlling are performed. In the step S6, the packet controlling is performed, and in the step S7, a system suspension processing are performed, thereby finishing the operation.

In the system suspension processing (step S7), a determination is performed as to whether t2=going-out time te (n) (the going-out-starting time tes (n) or the going-out-finishing time tee (n)) is abnormal (step S11). If the result is NO and there is no abnormality, a determination is performed as to whether t3=going-into time ti (n+1) (the going-into-starting time tis (n+1) or the going-into-finishing time tie (n+1)) is abnormal (step S12). If the result is NO and there is no abnormality, the operation returns to the step S11 so as to continue watching the occurrence of abnormality. On the other hand, if the result is YES in the step S11 or step S12 and there is any abnormality in t2 or t3, the suspension of inspection is instructed to the sampling control section 10 and the occurrence of abnormality is transmitted to the production controller 200 (step S13). The result of the determination of abnormality is recorded in the flag register 7a. At this time, the timer (3) is started (step S14) and then, it is determined as to whether the inspection should be restarted (step S15). If the result is YES and the inspection is restarted, the operation returns to the step S11. On the other hand, if the result is NO and the inspection is not restarted, it is determined by means of the timer (3) as to whether a predetermined time has elapsed (step S16). If the result is NO and the predetermined time has not yet elapsed, the system forces the operation bring into a state of standby until the predetermined time has elapsed. If the result is YES and the predetermined time has elapsed, the system-suspending procedure is executed (step S17), thereby finishing the operation.

Figure 12:
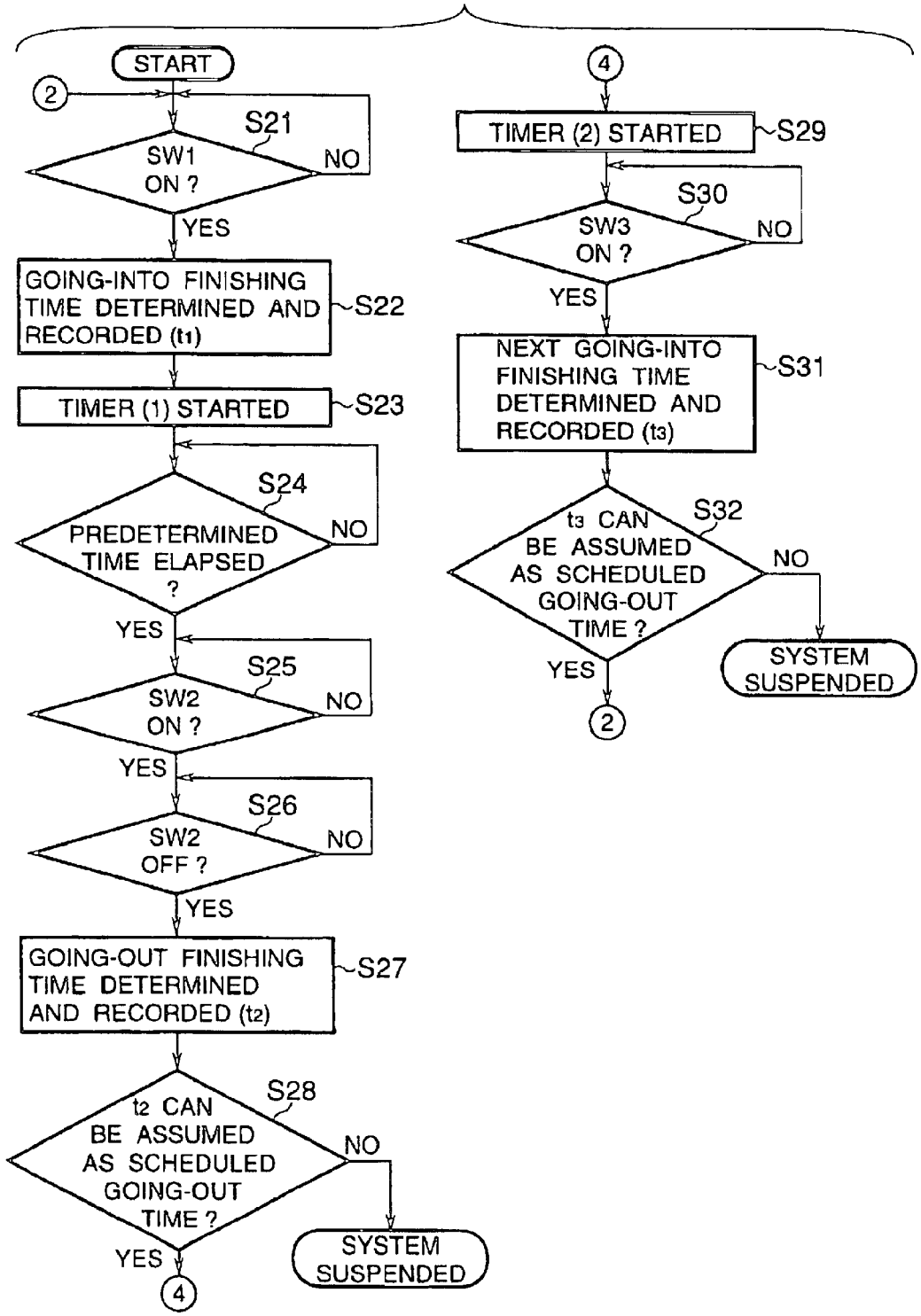
FIG. 12 is a flow chart indicating the operation of the board identification section.

FIG. 12 is a flow chart indicating the operation of the board identification section 4 (see FIG. 2). First of all, it is determined if the photoelectric switch SW1 is ON (step S21). If the result is NO and the photoelectric switch SW1 is not ON, the board identification section 4 forces the operation to bring into a state of standby until the photoelectric switch SW1 is turned ON. If the result is YES and the photoelectric switch SW1 is ON, a going-into time t1=ti(n) (the going-into-starting time tis (n) or the going-into-finishing time tie (n)) is determined and recorded (step S22) and the timer (1) is started (step S23). Then, it is determined as to whether a predetermined time corresponding to the time to the going-out has elapsed (step S24). If the result is NO and the predetermined time has not yet elapsed, the system forces the operation to bring into a state of standby until the predetermined time has elapsed. If the result is YES and the predetermined time has elapsed, it is determined as to whether the photoelectric switch SW2 is ON (step S25). If the result is NO and the photoelectric switch SW2 is not ON, the board identification section 4 forces the operation to bring into a state of standby until the photoelectric switch SW2 is turned ON. If the result is YES and the photoelectric switch SW2 is ON, it is then determined whether the photoelectric switch SW2 is turned OFF (step S26). If the result is NO and the photoelectric switch SW2 is not OFF, the board identification section 4 forces the operation to bring into a state of standby until the photoelectric switch SW2 is turned OFF. If the result is YES and the photoelectric switch SW2 is turned OFF, an going-out time t2=te(n) is determined and recorded (step S27). Then, a determination is made as to whether this t2 can be assumed as being the scheduled going out time (step S28). If the result is NO and this t2 cannot be assumed as being the scheduled going-out time, the operation is advanced to the system suspension (FIG. 11). If the result is YES and this t2 can be assumed as being the scheduled going-out time, the timer (2) is started (step S29). Next, it is determined as to whether the photoelectric switch SW3 is ON (step S30). If the result is NO and the photoelectric switch SW3 is not ON, the board identification section 4 forces the operation to bring into a state of standby until the photoelectric switch SW3 is turned ON. If the result is YES and the photoelectric switch SW3 is ON, the going-into time of the next process t3=ti(n+1) is determined and recorded (step S31). Then, a determination is made as to whether this t3 can be assumed as being the scheduled going-out time (step S32). If the result is NO and this t3 cannot be assumed as being the scheduled going-out time, the system is advanced to the system suspension (FIG. 11). If the result is YES and this t3 can be assumed as being the scheduled going-out time, the operation returns to the step S21.

Figure 13:
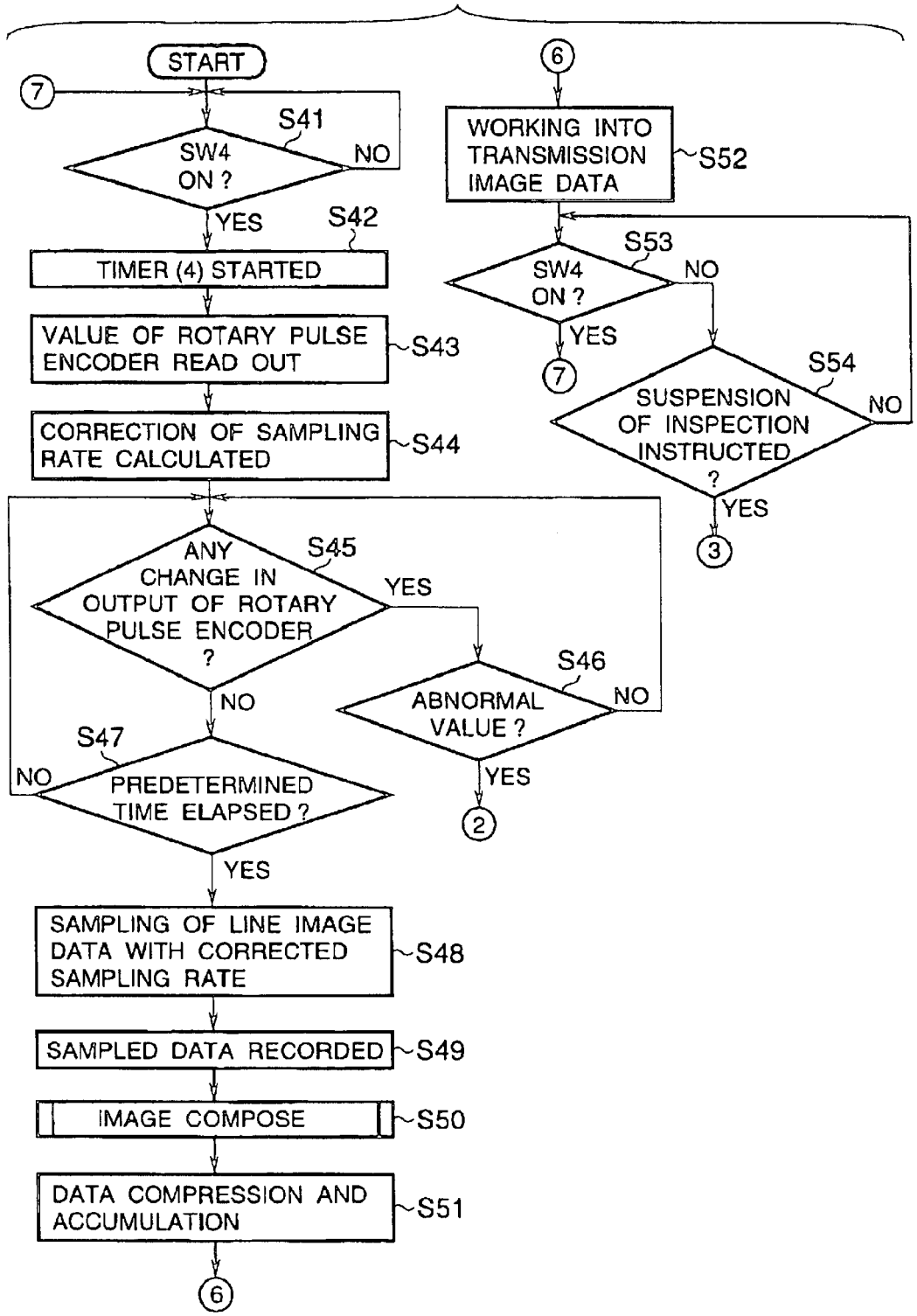
FIG. 13 is a flow chart indicating the operations of the image data sampling and that of the image compose control.

FIG. 13 is a flow chart indicating the operations of the image data sampling and that of the image compose control (see FIG. 3). First of all, it is determined if the leading end portion of the work board 1 has reached close to a position immediately below the CCD line sensor camera 11 by determining whether the photoelectric switch SW4 is ON (step S41). If the result is NO and the photoelectric switch SW4 is not ON, the system forces the operation to bring into a state of standby until the photoelectric switch SW4 is turned ON. If the result is YES and the photoelectric switch SW4 is ON, the timer (4) is started (step S42) and the value of the rotary pulse encoder 13 is read out (step S43). Based on this value, the correction of sampling rate is calculated (step S44) (FIG. 5) so as to determine if there is any change in the output value of the rotary pulse encoder 13 (step S45). If the result is YES and there is a change, it is then determined if this change is an abnormal value (step S46). If the result is YES and it is an abnormal value, the operation returns to the step S13 (FIG. 11). If the result is NO and it is not an abnormal value, the operation returns to the step S45. If the result is NO in the step S45 and there is no change in the output value, it is determined whether a predetermined time required for the passing of the work board 1 has elapsed (step S47). If the result is NO and the time is not yet elapsed, the operation goes back to the step S45. However, if the result is YES and the time has elapsed, the sampling of the line image data is performed at a corrected sampling rate (step S48) and the sampled data is recorded (step S49) (FIG. 4). After the image data is corrected and composed (step S50) (see FIGS. 6–8), the data is compressed so as to be stored in the hard disk HDD 16 (step S51). After a transmission image data has been processed (step S52), it is determined whether the photoelectric switch SW4 is turned OFF as a result of finishing of the passing of the work board 1 (step S53). If the result is OFF and the photoelectric switch SW4 is not turned OFF, a determination is made as to if there is an instruction to suspend the inspection from the main controlling section 70 of the production controller 200 (to be explained with reference to FIG. 17) (step S54). If the result is NO and there is no instruction to suspend the inspection, the operation returns to the step S53. If the result is YES and there is an instruction to suspend the inspection, the operation returns to the step S14 (FIG. 11). If the result is YES at the step S53 and the photoelectric switch SW4 is turned OFF, the operation returns to the step S41.

Figure 14:
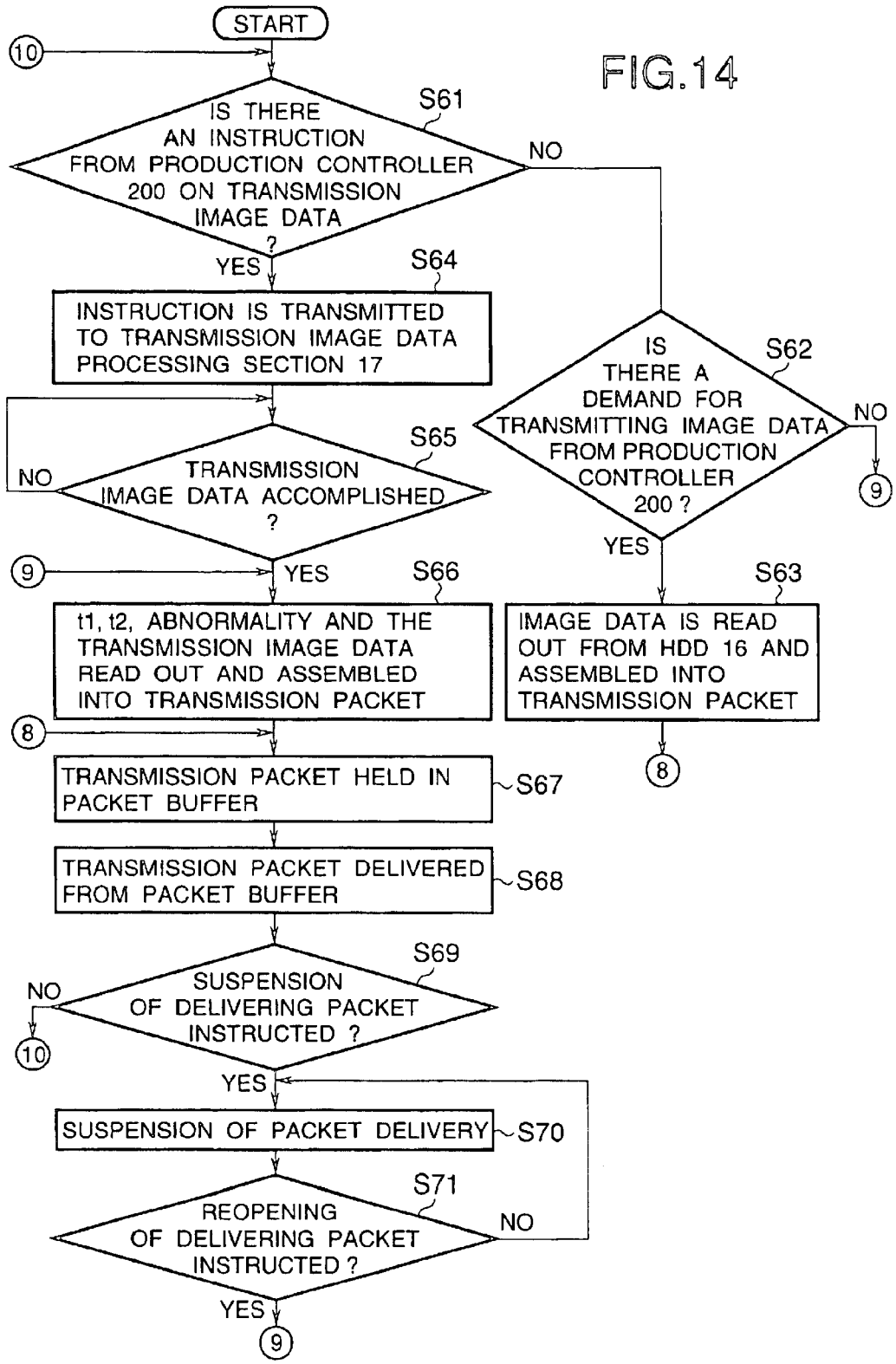
FIG. 14 is a flow chart indicating the operation of the packet control.

FIG. 14 is a flow chart indicating the operation of the packet control. First of all, it is determined if there has been an instruction from the production controller 200 about the transmission image data (step S61). If the result is NO, a determination is also made as to if there has been a demand for transmitting a detailed image data from the production controller 200 (step S62). If the result is NO, and there has been no demand for transmitting a detailed image data, the operation is advanced to the step S66. If the result is YES and there has been a demand for transmitting a detailed image data, a corresponding image data is read out from the hard disk HDD 16 and assembled into a transmission packet and then advanced to the step S67. If the result is YES in the step S61, the content of the instruction is transmitted to the transmission image data processing section 17 (step S64), and a determination is made as to if the processing of the transmission image data has been accomplished (step S65). If the result is NO and the processing of the transmission image data is not yet accomplished, the system forces the operation to bring into a state of standby until the processing is accomplished. If the result is YES and the processing of the transmission image data is already accomplished, the going-into time t1=ti(n), the going-out time t2=te(n), the existence or non-existence of abnormality and the transmission image data are read out and assembled into a transmission packet (step S66), which is then held in the packet buffer 19 (step S67). When an instruction is transmitted from the communication control section 27 to deliver the transmission packet, the transmission packet is delivered from the packet buffer 19 (step S68). At this moment, it is determined if there has been an instruction from the main control section 70 (to be explained with reference to FIG. 17) with regard to the suspension of delivering the packet (step S69). If the result is NO and there is no instruction to suspend the delivering of the packet, the operation returns to the initial step S61. If the result is YES and there has been an instruction to suspend the delivering of the packet, the delivering of the packet is suspended (step S70). Subsequently, a determination is made as to if there has been an instruction from the main control section 70 with regard to the restarting of the packet delivering (step S71). If the result is NO and there is no such an instruction, the operation returns to the step S70 so as to continue the suspension of the delivery. If the result is YES and there has been an instruction to restart the packet delivering, the operation returns to the step S66.

Figure 15:
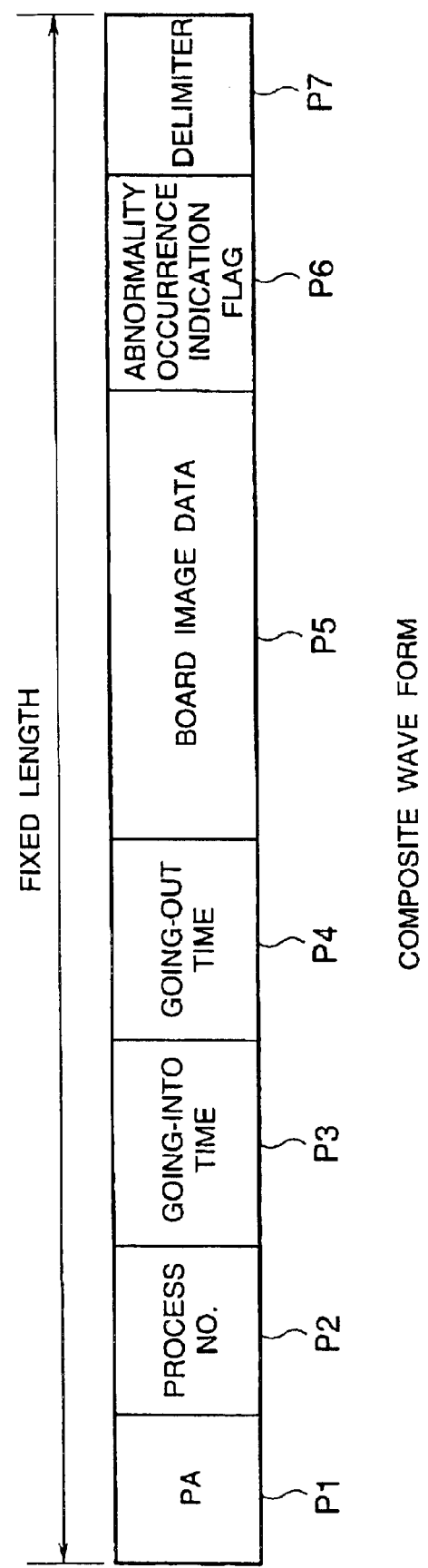
FIG. 15 is a diagram illustrating an example of the construction of the transmission packet.

FIG. 15 is a diagram illustrating an example of the construction of the transmission packet. This transmission packet is of fixed length and consists of the preamble (PA) P1, a process number P2, a process-going-into or entry time P3, a process-going-out or exit time P4, a board image data P5, an abnormality occurrence indication flag P6, and the delimiter P7.

Figure 16:
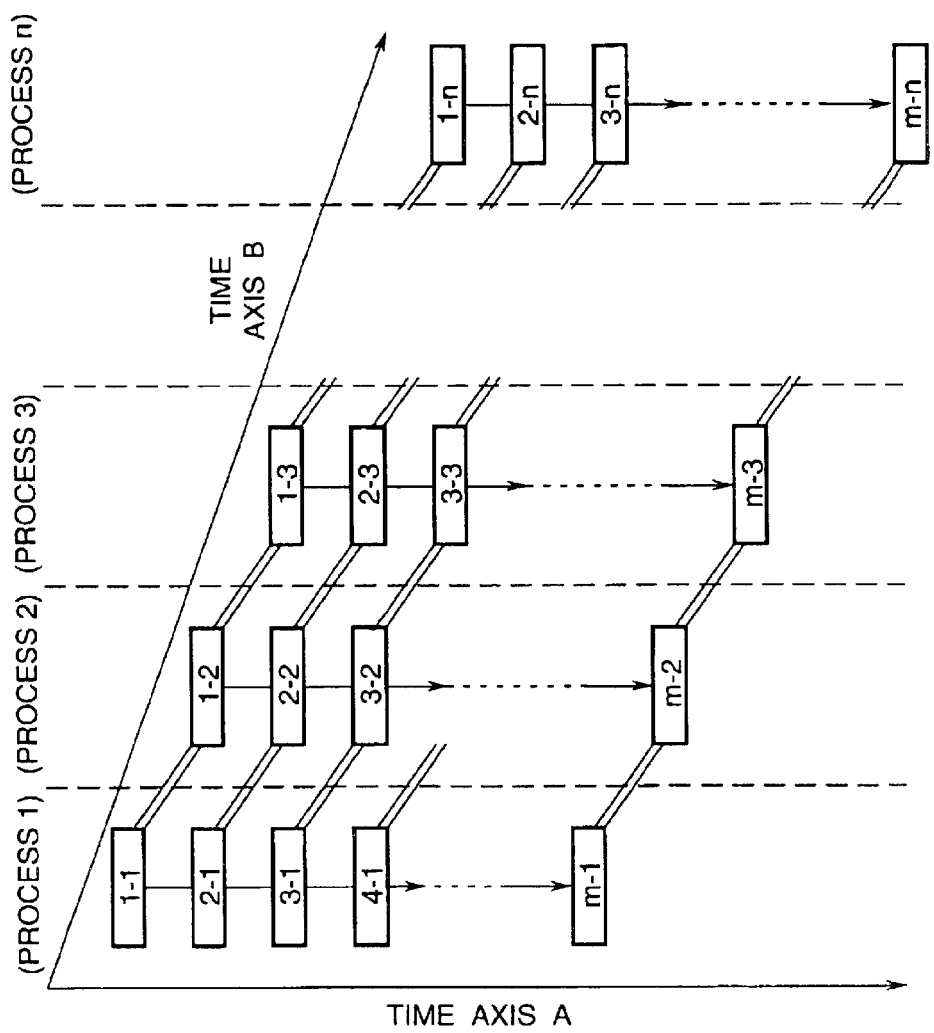
FIG. 16 is a diagram illustrating an entire sequence of each transmission packet.

FIG. 16 is a diagram illustrating an entire sequence of each transmission packet. In this case, the packet is represented by "provisional board number-process number". The time axis A indicates the position of the packet in a specific manufacturing process in which the work board 1 is transferred with time. For example, as indicated by "1-3", "2-3" and "3-3" in the manufacturing process 3, the work board having provisional numbers 1, 2 and 3 goes into and goes out from the manufacturing process 3 with time. Whereas the time axis B indicates the position of the packet as a specific work board 1 is transferred through each manufacturing process with time. For example, as indicated by "3-1", "3-2" and "3-3", the work board having a specific provisional number 3 enters and then exits each manufacturing process with time.

The time axis A extending in the vertical direction in one manufacturing process is independent from other manufacturing processes, so that there is no possibility that a plural number of work boards are placed on the same manufacturing process at the same moment, and hence, any of transmission packet would never overlap with another transmission packet on the same time axis A. With respect to the position of the transmission packet over the time axis B for each work board 1, since each work board is successively subjected to and gone out from each manufacturing process, the position of one transmission packet would never overlap with another transmission packet over the time axis B.

A medium which is capable of securing the elapsing of time of an electric signal can be served as a signal transmission line. Here, by the use of the time axis A and time axis B, the transmission packets each assigned to each work board 1 are placed along these independent time axes B, and each transmission-starting time is set at a point on the time axis A of the initial manufacturing process 1, thereby enabling to grasp the processing history of one work board as changes in surface board-working data.

In accordance with the aforementioned idea, a transmission channel is assigned to each work board 1, and the board image data that has been obtained and processed by each manufacturing process controller 100 is assembled into a packet, thus enabling to control the packet according to the assigned channel, thereby making it possible to transmit the processing history of individual work board 1 as an image data to a production controller which is located at a remote place. There is no possibility that each packet may overlap with other packet during this transmission period.

Figure 17:
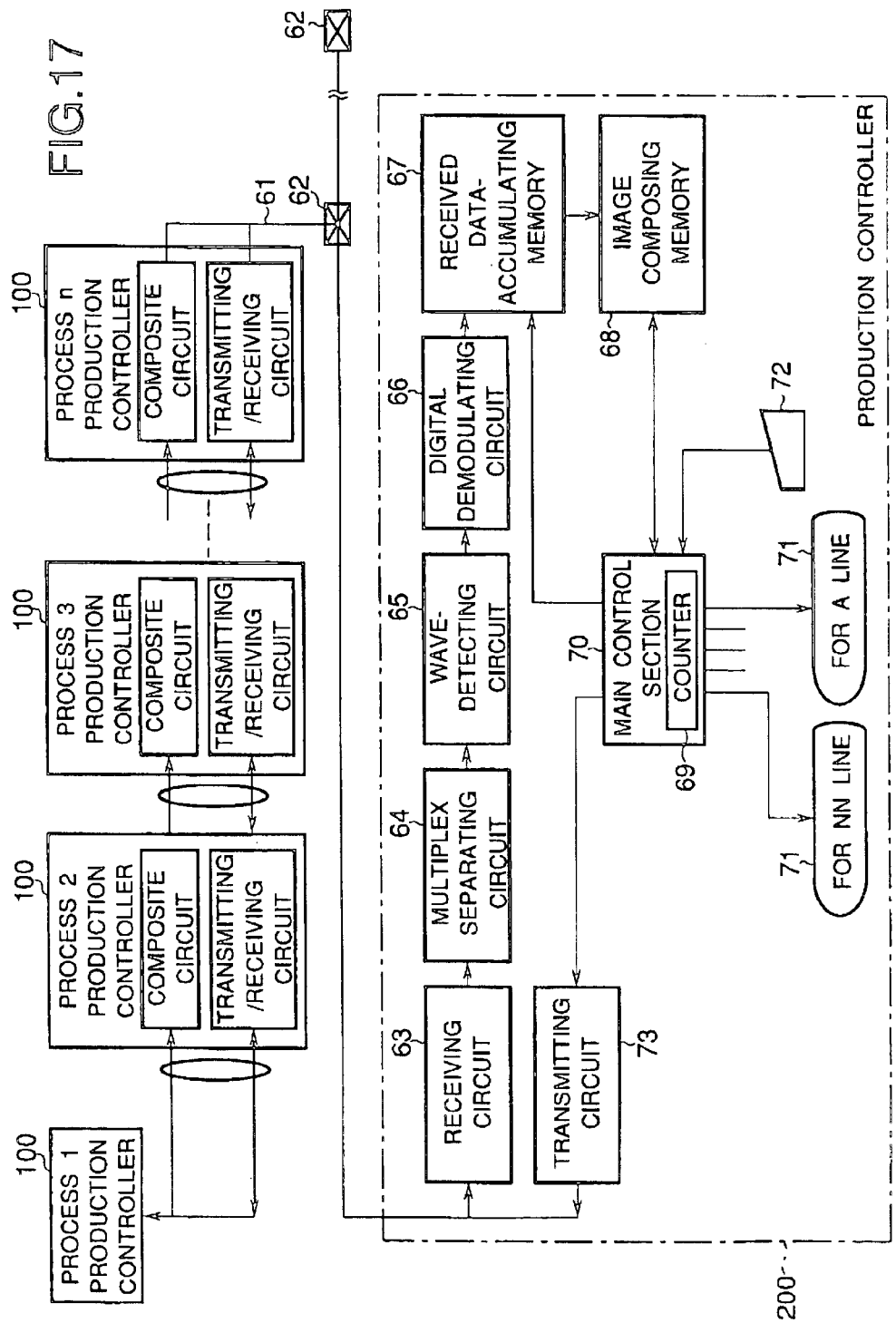
FIG. 17 is a block diagram illustrating the configurations of the transmission system and those of the production controller.

FIG. 17 is a block diagram illustrating the configurations of the transmission system and those of the production controller. Each manufacturing process controller 100 of the manufacturing processes (1) to (n) of the A production line is, for instance, connected with a multi-transmission line 61 using a coaxial cable, and further connected via a connector 62 with the production controller 200. On the occasion of transmitting a control data, a control channel Cch (bidirectional) will be used, whereas on the occasion of transmitting a packet data, a data channels ch1–chm will be used. The production controller 200 is provided with a receiving circuit 63 for receiving the packet, a multiplex-separating circuit 64 for separating the multiplexed data, wave-detecting circuit 65 for detecting the data signal, a digital demodulating circuit 66 for demodulating the data, a received data-accumulating memory 67 for accumulating the data, and an image composing memory 68 for composing and storing the data therein. The main control section 70 displays the composed image on the surface the display 71 (for A line to NN line) as required in accordance with the instruction from the key board 72. The control data is transmitted from the main control section 70 through a transmitting circuit 73 to a transmission line, and ultimately received by each manufacturing process controller 100.

Figure 18:
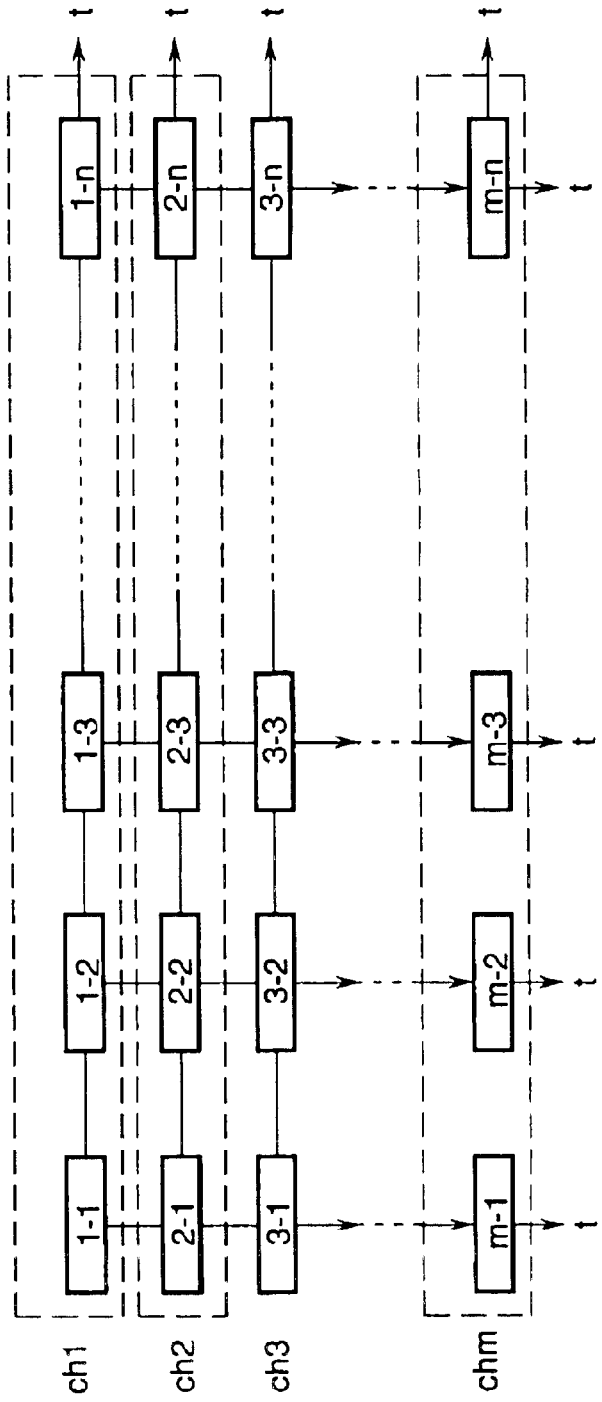
FIG. 18 is a diagram illustrating an image file to be accumulated in the received data accumulating memory.

FIG. 18 is a diagram illustrating an image file to be accumulated in the received data accumulating memory. In this case, although the data of each packet shown in FIG. 16 is basically accumulated in the receive a data accumulating memory 67, the preamble P1 and delimiter P7 are removed. The ch1 is used for accumulating the data of each manufacturing process 1, 2, - - - , n of the work board 1 having a provisional board number 1 in the memory as an image data file. Likewise, the ch2 is used for accumulating the data of each manufacturing process 1, 2, - - - , n of the work board 1 having a provisional board number 2 in the memory as an image data file 2.

Figure 19:
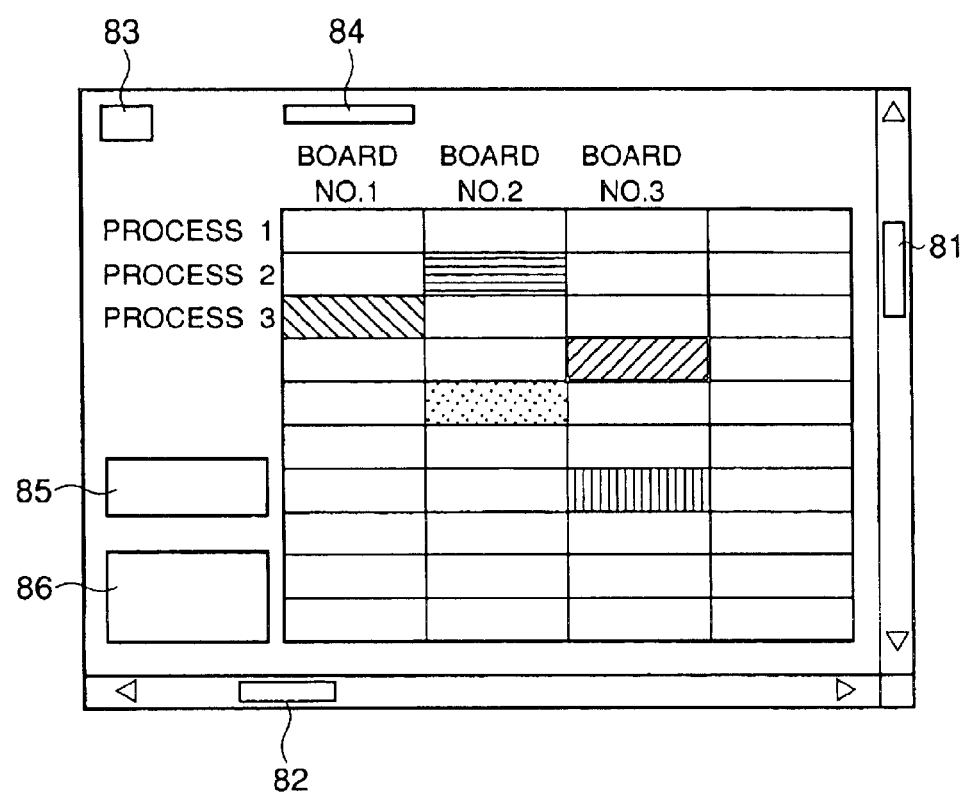
FIG. 19 is a diagram showing an example of displaying the image of work board in the display.

FIG. 19 is a diagram showing an example of displaying the image of work board in the display 71. The surface images in the processes 1, 2, 3, - - - of all of the work board to be inspected and having board number 1, 2, 3, - - - are allowed to be displayed on a single picture screen through the operation of a vertical scroll button 81 and a horizontal scroll button 82.

As a result, changes in external appearance of the work board processed or treated at each manufacturing process can be compared relative to each other, so that it becomes possible to detect any non-uniformity in external appearance of the work board that might be occurred due to the same repeated working process even if there has been no problem in the transferring of the work board. Therefore, information which is useful is obtained for accelerating the stabilization of the manufacturing process.

Further, since a defective work board 1 is encircled by a frame, for instance, in the display thereof, the location of manufacturing process as well as the time at which the abnormality was generated can be immediately recognized. A window 86 will be displayed at the left bottom corner of the display to display a going-out time of the work board. Thus, moving a cursor to the display portion of the work board 1, and clicking the mouse botton enables display of the exit time.

Furthermore, since a dialog box switch 83 for illustrating the operation menu is allocated, the operation menu can be displayed by clicking the switch 83. Thereafter, the portion of board image data transmission is selected from the menu and then, a desired display size in the submenu is selected, thereby allowing to transmit and display the desired JPEG data of the work board 1 that has been accumulated in the hard disk HDD 16 in the selected display size.

Additionally, a display title bar 84 such as "A production line" and a window 85 for displaying the number of work boards being processed or treated are also provided in the display 71.

Figure 20A:
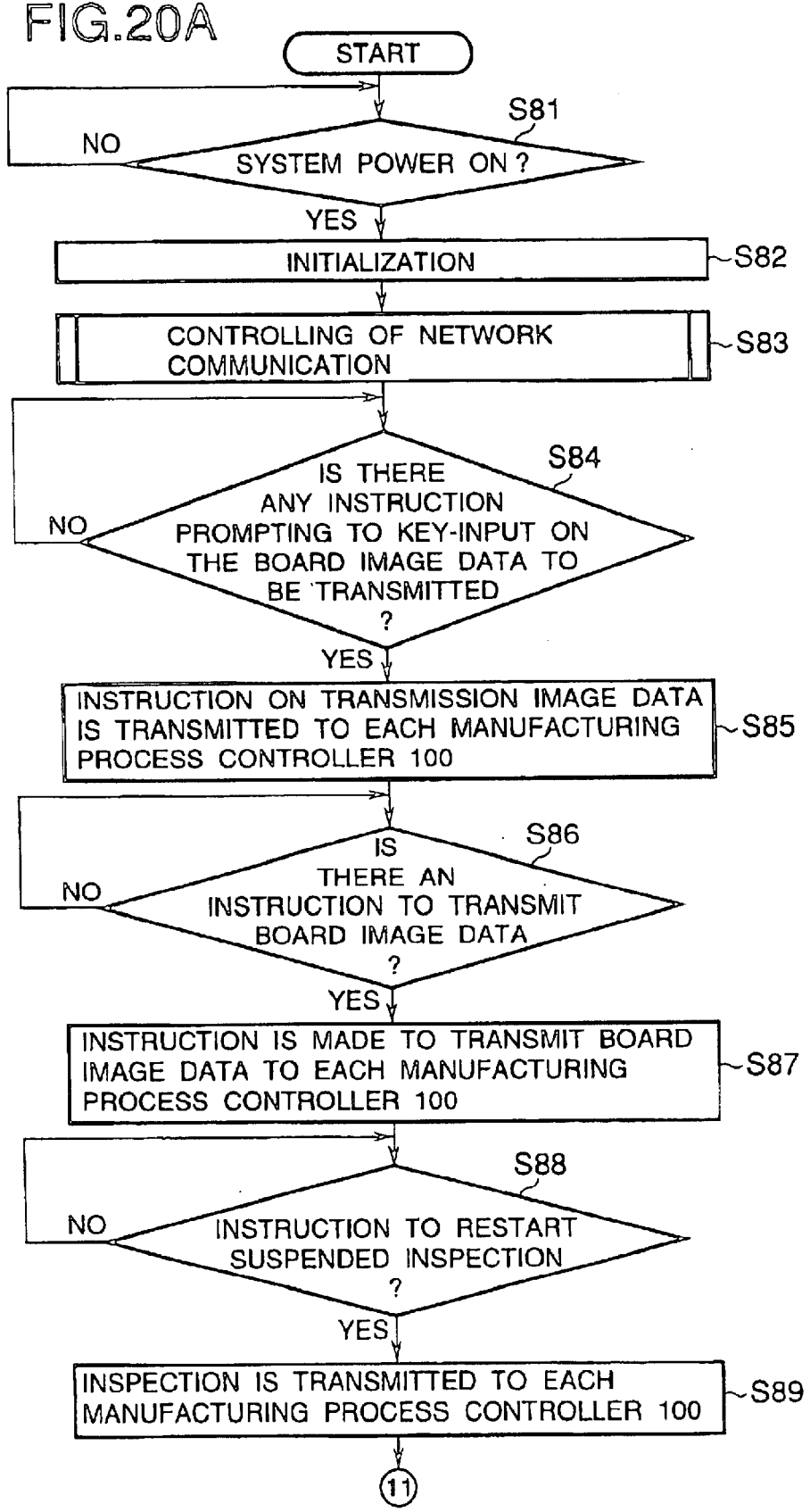
FIGS. 20 A, B, and C are a flow chart indicating the operation of the production controller in FIG. 1.

FIGS. 20 A, B, and C are flow charts indicating the operation of the production controller 200. First of all, a determination is made as to whether the system power source is ON (step S81). If the result is NO, the system forces the operation to bring into a state of standby until the power is turned ON. If the result is YES, the initialization of the system is performed (step S82).

In the next step S83, the controlling of network communication is performed. That is, in the step S84, it is determined if there is any instruction prompting to the key input on the board image data to be displayed. If the result is YES, an instruction on the transmission image data is transmitted to each manufacturing process controller 100 (step S85). If the result is NO, the operation returns the step S84. A determination is made as to if there is an instruction by the key input to transmit a detailed board image data, and if there is a key input by a user (step S86). If the result is NO, the system forces the operation to bring into a state of standby until the instruction is input. If the result is YES and there is the instruction by the key input, an instruction is given to transmit the detailed board image data to each manufacturing process controller 100 (step S87). Then, a determination is made as to if there is an instruction by the key input to restart the suspended inspection (step S88). If the result is NO, the system forces the operation to bring into a state of standby until the instruction is input. If the result is YES and there is the instruction, an instruction to restart the inspection is transmitted to each manufacturing process controller 100 (step S89). In the step S90, a determination is made as to whether the transmission packet is received from the manufacturing process controller 100. If the result is NO, the operation is advanced to the step S95. If the result is YES and the transmission packet is received, the counter 69 is count up (step S91) and the transmission packet is stored as an image file at the predetermined portion of the received data-accumulating memory 67 (step S92). Thereafter, the image file is read out to compose it into a display image (step S93) which is then displayed in the display 71 (step S94). In the step S95. a determination is made as to whether the transmission packet of the JPEG file is received from the manufacturing process controller 100. If the result is NO, the operation returns to the step S90. If the result is YES and the transmission packet is received, the transmission packet is stored as a JPEG file in the received data-accumulating memory 67 (step S96). Thereafter, the JPEG file is read out to compose it into a display image (step S97) which is then displayed in the display 71 (step S98). Further, the number of work boards being treated is displayed in the display window 85 (step S99) and a determination is made as to whether the system operation should be suspended (step S100). If the result is NO, the operation of the system is continued. If the result is YES, the suspension of the system is executed (step S101), thereby finishing the operation.

It should be understood that the present invention is not limited to the above embodiments.

For example, instead of individually assigning the transmission channel to each work board, the transmission channel may be assigned to each working process.

Further, the work material includes any kind of furniture boards and doors.

As explained above, according to the present invention, since the sampling of line sensor is controlled by measuring the moving velocity of the work board, it is possible to obtain, at a high resolution, an image data of work board moving along a processing line by the use of a line sensor.

Further, according to the present invention, it is possible to distinguish an individual work board which is inherently difficult to distinguish from the others by the external appearance thereof, so that it is possible to accurately grasp the progress of working, i.e. the position of individual work board in relative to the manufacturing process. Even if a defect is found after the delivery of finished board, the manufacturing conditions thereof can be traced in detail, since it is possible to find out the accurate time when this defective product was being moved through any one of the manufacturing processes thereof.

All publications, patents and patent applications cited herein are incorporated herein by reference in their entirety.

What is claimed is:

1. A surface inspection system for work boards passing through a plurality of manufacturing processes being transferred by a transferring roller, comprising:

a detecting means for detecting entry and exit of each work board into and out of each manufacturing process;

a time-measuring means for measuring times when the entry and exit of each work board are detected by said detecting means;

a determining means for determining whether each work board exits out of each manufacturing process at a scheduled exit time calculated based on the entry time measured by said time-measuring means;

line sensors for one dimensionally acquiring image data related to colors of an elongated work board having exited out of each manufacturing process in lines perpendicular to the moving direction of the work board, each line sensor comprising two types of image data sampling means, one for an odd-number sampling line and the other for an even-number sampling line;

a velocity-measuring means for measuring in real time the rotational velocity of the transferring roller on each data sampling position of the line sensor;

a sampling control means for controlling timing of the image data sampling of said line sensor in the direction of board movement and on the basis of the moving velocity of the work board measured by said velocity-measuring means;

an image-composing memory for forming a two-dimensional image of the work board by sequentially combining odd line data and even-line data from the line sensor;

a controlling means to correct the image data based on degree of slant of the work board;

an identifying means for identifying the work board and the image data thereof based on a process number representing each manufacturing process, and on times of entry and exit of the work board into and out of the process measured by said time-measuring means; and a transmitting means for assigning each work board its own transmission channel for sequentially transmitting images of the board on each manufacturing process, assembling said image data into a transmission packet and transmitting said transmission packet.

2. A surface inspection system as in claim 1, wherein slant correction is accomplished by an affine transformation based on the angle of slant as determined by the following equation:

$$\theta = \cos^{-1}(A_0/A')$$

wherein $\theta$ equals the angle of slant, $A_0$ equals the number of pixels corresponding to the width of the work board and $A'$ equals the number of pixels forming the board on the data sampling line.

* * * * *